United States Patent
Mumm et al.

(10) Patent No.: US 9,823,255 B2
(45) Date of Patent: Nov. 21, 2017

(54) METHOD FOR ASSESSING PROTEIN IDENTITY AND STABILITY

(71) Applicant: ARMO BioSciences, Inc., Redwood City, CA (US)

(72) Inventors: John Brian Mumm, Los Altos Hills, CA (US); Peter Van Vlasselaer, Woodside, CA (US)

(73) Assignee: ARMO BioSciences, Inc., Redwood City, CA (US)

( * ) Notice: Subject to any disclaimer, the term of this patent is extended or adjusted under 35 U.S.C. 154(b) by 0 days.

(21) Appl. No.: 14/895,880

(22) PCT Filed: Jun. 13, 2014

(86) PCT No.: PCT/US2014/042399
§ 371 (c)(1),
(2) Date: Dec. 3, 2015

(87) PCT Pub. No.: WO2014/204816
PCT Pub. Date: Dec. 24, 2014

(65) Prior Publication Data
US 2016/0123991 A1   May 5, 2016

Related U.S. Application Data

(60) Provisional application No. 61/836,034, filed on Jun. 17, 2013.

(51) Int. Cl.
| | | |
|---|---|---|
| *A61K 38/00* | (2006.01) | |
| *C07K 1/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *G01N 33/68* | (2006.01) | |
| *G01N 27/447* | (2006.01) | |
| *G01N 30/88* | (2006.01) | |

(52) U.S. Cl.
CPC ..... *G01N 33/6869* (2013.01); *G01N 33/6848* (2013.01); *G01N 33/6851* (2013.01); *G01N 27/447* (2013.01); *G01N 2030/8831* (2013.01); *G01N 2333/5428* (2013.01); *G01N 2496/00* (2013.01); *G01N 2560/00* (2013.01)

(58) Field of Classification Search
CPC ....... G01N 33/6851; G01N 2030/8831; G01N 2333/5428; G01N 2496/00; G01N 2560/00; G01N 27/447; G01N 33/6848; G01N 33/6869; G03F 1/46; G03F 1/54; G03F 1/50
See application file for complete search history.

(56) References Cited

U.S. PATENT DOCUMENTS

| | | |
|---|---|---|
| 5,231,012 A | 7/1993 | Mosmann et al. |
| 5,252,714 A | 10/1993 | Harris et al. |
| 5,328,989 A | 7/1994 | Vellekamp et al. |
| 5,624,823 A | 4/1997 | Sachs et al. |
| 5,643,575 A | 7/1997 | Martinez et al. |
| 5,665,345 A | 9/1997 | Yarchoan et al. |
| 5,710,251 A | 1/1998 | Vellekamp et al. |
| 5,824,784 A | 10/1998 | Kinstler et al. |
| 5,866,134 A | 2/1999 | Fine et al. |
| 5,876,969 A | 3/1999 | Fleer et al. |
| 5,908,621 A | 6/1999 | Glue et al. |
| 5,919,455 A | 7/1999 | Greenwald et al. |
| 5,932,462 A | 8/1999 | Harris et al. |
| 5,945,097 A | 8/1999 | Cutler |
| 5,951,974 A | 9/1999 | Gilbert et al. |
| 5,985,263 A | 11/1999 | Lee et al. |
| 5,985,265 A | 11/1999 | Kinstler et al. |
| 5,985,857 A | 11/1999 | Hudson et al. |
| 5,989,867 A | 11/1999 | Knappe et al. |
| 6,217,857 B1 | 4/2001 | Mosmann et al. |
| 6,387,364 B1 | 5/2002 | Ferguson |
| 6,428,985 B1 | 8/2002 | Bromberg et al. |
| 6,660,258 B1 | 12/2003 | Tovey |
| 6,770,272 B2 | 8/2004 | Strom et al. |
| 6,989,377 B2 | 1/2006 | Hayes et al. |
| 7,052,684 B2 | 5/2006 | Ferguson |

(Continued)

FOREIGN PATENT DOCUMENTS

| | | |
|---|---|---|
| CN | 1760209 | 10/2004 |
| CN | 102145178 | 8/2011 |

(Continued)

OTHER PUBLICATIONS

Payne et al. Product development issues for PEGylated proteins. Pharma Dev Technol 2011, vol. 16, No. 5, pp. 423-440.*
Soderquist et al. PEGylation of interleukin-10 for the mitigation of enhanced pain states. J Biomed Mater Res A. 2010. vol. 3, No. 93, pp. 1169-1179.*
Cindric, et al., (2007) "Structural 1-16 characterization of PEGylated rHuG-CSf and location of PEG attachment sites". Journal of Pharmaceutical and Biomedical Analysis. New York. NY. US, 44(2):388-395.
Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.

(Continued)

*Primary Examiner* — Marcela M Cordero Garcia
(74) *Attorney, Agent, or Firm* — Carol L. Francis; Bozicevic, Field & Francis LLP

(57) ABSTRACT

The present invention relates to methods and other technologies that may be used to determine whether compositions (e.g., pharmaceutical compositions) comprising interleukin-10 molecules (e.g., pegylated interleukin-10) meet particular product-related specifications prior to being administered to a subject for the treatment and/or prevention of the diseases, disorders and conditions, and/or the symptoms thereof, described herein.

5 Claims, 6 Drawing Sheets

(56) References Cited

U.S. PATENT DOCUMENTS

| | | | |
|---|---|---|---|
| 7,052,686 B2 * | 5/2006 | Lee | A61K 47/48215 424/78.3 |
| 7,056,701 B2 | 6/2006 | Fleer et al. | |
| 7,261,882 B2 | 8/2007 | Watkins | |
| 7,611,700 B2 | 11/2009 | Gantier et al. | |
| 7,650,243 B2 | 1/2010 | Gantier et al. | |
| 7,666,400 B2 | 2/2010 | Chang et al. | |
| 7,749,490 B2 | 7/2010 | Sommer et al. | |
| 7,939,056 B2 | 5/2011 | Horwitz et al. | |
| 8,044,175 B2 | 10/2011 | Dransfield et al. | |
| 8,067,532 B2 | 11/2011 | MacLean | |
| 8,618,256 B2 | 12/2013 | Cox | |
| 2002/0044921 A1 | 4/2002 | Lee et al. | |
| 2003/0012775 A1 | 1/2003 | Brandt et al. | |
| 2003/0186386 A1 | 10/2003 | Hansen et al. | |
| 2004/0213795 A1 | 10/2004 | Collins et al. | |
| 2005/0008615 A1 | 1/2005 | Bam et al. | |
| 2005/0260767 A1 | 11/2005 | Clerici et al. | |
| 2006/0046961 A1 | 3/2006 | McKay et al. | |
| 2006/0210534 A1 | 9/2006 | Lee et al. | |
| 2006/0258607 A1 | 11/2006 | Jarosch et al. | |
| 2007/0134197 A1 | 6/2007 | Eichner et al. | |
| 2008/0058246 A1 | 3/2008 | Bhaskaran et al. | |
| 2008/0069797 A1 | 3/2008 | Roncarolo et al. | |
| 2008/0081031 A1 | 4/2008 | Oft et al. | |
| 2008/0096252 A1 | 4/2008 | Zamost et al. | |
| 2009/0035256 A1 | 2/2009 | Sommer et al. | |
| 2009/0214463 A1 | 8/2009 | Slobedman et al. | |
| 2009/0214471 A1 | 8/2009 | Oft et al. | |
| 2010/0068147 A1 | 3/2010 | Hibberd et al. | |
| 2010/0111898 A1 | 5/2010 | Pelura | |
| 2010/0129386 A1 | 5/2010 | Elson et al. | |
| 2010/0255496 A1 | 10/2010 | Schrader et al. | |
| 2010/0266532 A1 | 10/2010 | Ferguson | |
| 2010/0297070 A1 | 11/2010 | Dugan et al. | |
| 2011/0064690 A1 | 3/2011 | Lee et al. | |
| 2011/0091419 A1 | 4/2011 | Oft et al. | |
| 2011/0250163 A1 | 10/2011 | Blaisdell et al. | |
| 2011/0275123 A1 | 11/2011 | Paciotti et al. | |
| 2011/0305665 A1 | 12/2011 | Lee et al. | |
| 2011/0312010 A1 | 12/2011 | Manuilov et al. | |
| 2012/0003221 A1 | 1/2012 | McDonagh et al. | |
| 2012/0115926 A1 | 5/2012 | Geary et al. | |
| 2012/0213793 A1 | 8/2012 | Huang et al. | |
| 2012/0252742 A1 | 10/2012 | Kranz et al. | |
| 2012/0270899 A1 | 10/2012 | Bannister et al. | |
| 2012/0321617 A1 | 12/2012 | Osterroth et al. | |
| 2013/0156774 A1 | 6/2013 | Kuchroo et al. | |
| 2014/0199750 A1 | 7/2014 | Weng et al. | |
| 2014/0256626 A1 | 9/2014 | Santi et al. | |
| 2014/0314795 A1 | 10/2014 | Riddell et al. | |
| 2014/0349402 A1 | 11/2014 | Cooper et al. | |
| 2015/0038678 A1 | 2/2015 | Eaton et al. | |
| 2015/0118244 A1 | 4/2015 | Shahabi et al. | |
| 2016/0340406 A1 | 11/2016 | Zhao et al. | |
| 2016/0361415 A1 | 12/2016 | Mumm et al. | |
| 2016/0375101 A1 | 12/2016 | Oft | |

FOREIGN PATENT DOCUMENTS

| | | | |
|---|---|---|---|
| EP | 0251304 | 1/1988 | |
| EP | 2066336 | 9/2012 | |
| WO | WO 92/12725 | 8/1992 | |
| WO | WO 92/12726 | 8/1992 | |
| WO | 95/03411 | 2/1995 | |
| WO | 9503411 | 2/1995 | |
| WO | WO 95/06058 | 3/1995 | |
| WO | WO 95/19780 | 7/1995 | |
| WO | WO 96/11953 | 4/1996 | |
| WO | WO 97/03690 | 2/1997 | |
| WO | WO 99/32134 | 7/1999 | |
| WO | WO 01/05821 | 1/2001 | |
| WO | WO 01/58950 | 8/2001 | |
| WO | WO02/26265 | * 4/2002 | A61K 47/48 |
| WO | WO 02/26265 | 4/2002 | |
| WO | WO 2004/044006 | 5/2004 | |
| WO | WO 2004/056850 | 7/2004 | |
| WO | WO 2006/075138 | 7/2006 | |
| WO | WO 2006/119170 | 11/2006 | |
| WO | WO 2008/054585 | 5/2008 | |
| WO | WO 2009/016043 | 2/2009 | |
| WO | 2009036568 | 3/2009 | |
| WO | WO 2010/077853 | 7/2010 | |
| WO | WO2010/077853 | * 7/2010 | A61K 47/48 |
| WO | WO 2011/051489 | 5/2011 | |
| WO | WO 2012/004384 | 1/2012 | |
| WO | WO 2012/050923 | 4/2012 | |
| WO | WO 2012/050930 | 4/2012 | |
| WO | WO 2013/113008 | 8/2013 | |
| WO | 2014172392 | 10/2014 | |
| WO | 2015070060 | 5/2015 | |
| WO | 2015153753 | 10/2015 | |

OTHER PUBLICATIONS

Mattos et al.,(2012) "11 PEGylation of interleukin-10 improves the pharmacokinetic profile and enhances the antifibrotic effectivity in eel-induced fibrogenesis in mice", Journal of Controlled Release, Elsevier, Amsterdam, NL, 162(I):84-91.

Gargett et al., (2015) "Different cytokine and stimul ation conditions influence t he expansion and immune phenotype of third-generat ion chimeric antigen receptor T cells specific for tumor antigen GD2", Cytotherapy, 17(4):487-495.

Gill et al., (2015) "Going viral: Chimericantigen receptor T-cell therapy forhematological malignancies", Immunological Reviews 28150181 Blackwell Publishing Ltd GBR, 263(1):68-89.

Teng et al., (2011) "Stable IL-10: A new therapeutic that promotes tumor immunity" Cancer Cell 2011 Cell Press USA, 20(6):691-693.

Mumm et al. (2011) "IL-10 elicits IFNγ-dependent tumor immune surveillance," Cancer Cell; 20(6):781-796.

Accession NP_036986.2; GI 148747382; Aug. 10, 2014.

Accession NP_776513.1; GI 41386772; Jan. 4, 2015.

Accession NP_001009327.1; GI 57164347; Feb. 13, 2011.

Accession ABY86619.1; GI 166244598 ; Aug. 4, 2008.

Accession AAC23839.1; GI 3242896; Jun. 8, 2000.

"Guidance for Industry Immunogenicity Assessment for Therapeutic Protein Products," (2013) FDA Guidances.

"Highlights of Prescribing Information," (1997) Rituxan.

Recombinant Human IL-1 0 Protein, CF R&D Systems, accessed Feb. 22, 2016.

Recombinant Mouse I L -1 0 Protein R&D Systems, accessed Feb. 22, 2016.

Agata et al. (1996) "Expression of the PD-1 antigen on the surface of stimulated mouse T and B lymphocytes," Int Immunol; 8(5):765-772.

Aggen (2010) "Engineering Human Single-Chain T Cell Receptors," Dissertation; http://hdl.handle.net/2142/18585.

Alvarez et al. (2012) "Effects of PEGylation and Immune Complex Formation on the Pharmacokinetics and Biodistribution of Recombinant Interleukin10 in Mice," Drug Metab Dispos; 40(2):360-373.

Ansari and Raghava (2010) "Identification of conformational B-cell Epitopes in an antigen from its primary sequence," Immunome Res; 6:9pgs.

Ansell et al. (2002) "Phase 1 study of interleukin-12 in combination with rituximab in patients with B-cell non-Hodgkin lymphoma," Blood; 99:67-74.

Arakawa and Tsumoto (2003) "The effects of arginine on refolding of aggregated proteins: not facilitate refolding, but suppress aggregation," Biochemical and Biophysical Research Communications; 304:148-152.

Armstrong et al. (1996) "Interleukin 10 (IL- 10) regulation of tumour necrosis factor cx (TNF-cx) from human alveolar macrophages and peripheral blood monocytes," Thorax; 51:143-149.

Asadullah et al. (1999) "Interleukin 10 Treatment of Psoriasis," Arch Dermatol.; 135-187-192.

(56) References Cited

OTHER PUBLICATIONS

Asadullah et al. (2003) "Interleukin 10 Therapy—Review of a New Approach," *Pharmacol. Rev.*; 55-241-269.
Bajetta et al. (1998) "Pilot Study of Subcutaneous Recombinant Human Interleukin 12 in Metastatic Melanoma," *Clinical Cancer Research*; 4:75-85.
Banerjee et al. (2012) "Poly(ethylene glycol)-Prodrug Conjugates: Concept, Design, and Applications," *Journal of Drug Delivery*; Article ID 103973:17 pages.
Bea at al. (2011) "Performance Evaluation of a Multiplex Assay for Future Use in Biomarker Discovery Efforts to Predict Body Composition," *Clin Chem Lab Med.*; 49(5):817-824.
Berger et al. (2009) "Safety and immunologic effects of IL-15 administration in nonhuman primates," *Blood*; 114:2417-2426.
Berman et al. (1996) "Systemic administration of cellular IL-10 induces an effective, specific, and long-lived immune response against established tumors in mice," *J Immunol*; 157:231-238.
Bilzer et al. (2006) "Role of Kupffer cells in host defense and liver disease," *Liver International*; 26:1175-1186.
Biswas et al. (2007) "Pathogen_specific CD8 T Cell Responses are Directly Inhibited by IL-10," *J Immunol.*; 179:4520-4528.
Brady et al. (1994) "Reflections on a peptide," *Nature*; 368:692-693.
Brooks et al. (2008) "IL-10 and PD-L1 operate through distinct pathways to suppress T-cell activity during persistent viral infection," *PNAS*; 105(51):20428-20433.
Burgess (2009) "Refolding Solubilized Inclusion Body Proteins," *Methods in Enzymology*; 463:259-282.
Cai et al. (1999) "IL-10 enhances NK cell proliferation, cytotoxicity and production of IFN-q when combined with IL-18," *Eur. J. Immunol.*; 29:2658-2665.
Caliceti et al. (2012) "Effect of Plasma Membrane Cholesterol Depletion on Glucose Transport Regulation in Leukemia Cells," *PLoS One*; 7:e41246.
Cannistra & Niloff (1996) "Cancer of the uterine cervix," *New Eng I J Med* 334:1030-1038.
Cao et al. (2011) "Janus kinase activation by cytokine oncostatin M decreases PCSK9 expression in liver cells," *J Lipid Res.*; 52(3):513-530.
Capitini et al. (2009) "Modulating T cell Homeostasis with IL-7: Preclinical and Clinical Studies," *J Intern Med*; 266(2):141-153.
Cebon et al. (2003) "Two phase I studies of low dose recombinant human IL-12 with Melan-A and influenza peptides in subjects with advanced malignant melanoma," *Cancer Immunity*; 3:7 (18 pages).
Chamow et al. (1994) "Modification of CD4 Immunoadhesin with Monomethoxypoly(ethylene glycol) Aldehyde via Reductive Alkylation," *Bioconjugate Chern.*; 5:133-140.
Chan et al. (2015) "The Potentiation of IFN-γ and Induction of Cytotoxic Proteins by Pegylated IL-10 in Human CD8 T Cells," *J Interferon Cytokine Res*; 35(12):948-955.
Chen & Zlotnik (1991) "IL-10: a novel cytotoxic T cell differentiation factor," *J Immunol*; 147:528-534.
Chen et al. (2007) "Prediction of linear B-cell epitopes using amino acid pair antigenicity scale," *Amino Acids*; 33:423-428.
Choi et al. (2006) "Serum adiponectin, interleukin-10 levels and inflammatory markers in the metabolic 1-18 syndrome," *Diabetes Research and Clinical Practice*; 75:235-240.
Collins et al. (2012) "Trastuzumab induces antibody-dependent cellmediated cytotoxicity (ADCC) in HER-2-non-amplified breast cancer cell lines," *Annals of Oncology*; 23:1788-1795.
Compton et al. (2004) "Pathogenesis of Enterotropic Mouse Hepatitis Virus in Immunocompetent and Immunodeficient Mice," *Comparative Medicine*; 54(6):681-689.
Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," *Journal of Clinical Oncology*; 33(1):74-82.

Couder et al. (1993) "Synthesis and biological activities of ψ(CH2NH) pseudopeptide analogues of the C-terminal hexapeptide of neurotensin," *Int. J. Peptide Protein Res.*; 41:181-184.
D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells," *J. Exp. Med*; 178:1041-1048.
Das et al. (2012) "IL-10—Producing Regulatory B Cells in the Pathogenesis of Chronic Hepatitis B Virus Infection," *J. Immunol.*; 189(8):3925-3935.
Davidson & Diamond (2001) "Autoimmune diseases," *New Engl J Med*; 345:340-350.
De Waal Malefyt et al. (1991) "Interleukin 10 (IL-10) and viral IL-10 strongly reduce antigen-specific human T cell proliferation by diminishing the antigen-presenting capacity of monocytes via downregulation of class II major histocompatibility complex expression," *J Exp Med*; 174(4):915-924.
De Waal Malefyt et al. (1991) "Interleukin 10(IL-10) Inhibits Cytokine Synthesis by Human Monocytes: An Autoregulatory Role of IL-10 Produced by Monocytes," *J. Exp. Med*; 174:1209-1220.
Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)," *J. Biol. Chem.*; 288:10805-10818.
Dolgin (2011) "Trial puts niacin—and cholesterol dogma—in the line of fire," *Natue Medicine*; 17(7):356.
Dorner et al. (2011) "A genetically humanized mouse model for hepatitis C virus infection," *Nature*; 474:208-211.
Easy Surf. Blood Volume Calculator [online]Oct. 1, 2012 [retrieved Aug. 18, 2014]. Available on the internet: <URL: https://web.archive.org/web/20121 001142649/http://www.easysurf.cc/cnver22.htm >.
Ehrilich et al. (2013) "Preparation and Characterization of Albumin Conjugates of a Truncated Peptide YY Analogue for Half-Life Extension," *Bioconjug. Chem.*; 24(12):2015-2024.
El-Manzalawy et al. (2008) "Predicting linear B-cell epitopes using string kernels," *J Mol Recognit*; 21:243-255.
Emmerich et al. (2012) "IL-10 directly activates and expands tumor-resident CD8(+) T cells without de novo infiltration from secondary lymphoid organs," *Cancer Res*; 72(14):3570-3581.
Engel et al. (2006) "Using Endoproteinases Asp-N and Glu-C to Improve Protein th Characterization," *Promega Corporation*; 10th edition.
Enzinger & Mayer (2003) "Esophageal cancer," *New Eng I J Med*; 349:2241-2252.
Fahnert et al. (2012) "Using Folding Promoting Agents in Recombinant Protein Production: A Review," *Methods inn Molecular Biology*; 824:3-36.
Fang et al. (2015) "Programmed Death 1 (PD-1) is involved in the development of proliferative diabetic retinopathy by mediating activation-induced apoptosis," *Mol Vis*; 21:901-910.
Farrar et al. (1999) "Cancer dormancy. VII. A regulatory role for COB+ T cells and IFN-gamma in establishing and maintaining the tumor-dormant state," *J Imunol* 162:2842-2849.
Fehniger and Caligiuri (2001) "Interleukin 15: biology and relevance to human disease," *Blood*; 97:14-32.
Feingold et al. (1996) "Endotoxin, TNF, and IL-I decrease cholesterol 7a-hydroxylase mRNA levels and activity," *Journ of Lipid Res*; 37:223-228.
Fiorentino et al. (1989) "Two types of mouse T helper cell. IV. Th2 clones secrete a factor that inhibits cytokine production by Th1 clones," *J Exp Med*; 170:2081-2095.
Forastiere et al. (2001) "Head and neck cancer," *New Engl J Med* 345:1890-1900.
Fridman et al. (2012) "The immune contexture in human tumours: impact on clinical outcome," *Nature*; 12:298-306.
Fry and Mackall (2002) "Interleukin-7: from bench to clinic," *Blood*; 99:3892-3904.
Fujiwara et al. (2010) "Extraction and purification of human interleukin-10 from transgenic rice seeds," *Protein Expression and Purification*; 72:125-130.

(56) References Cited

OTHER PUBLICATIONS

Galon et al. (2013) "The Continuum of Cancer Immunosurveillance: Prognostic, Predictive, and Mechanistic Signatures," *Immunity*; 39:11-26.
Gameren et al. (1994) "Effects of Recombinant human interleukin-6 in cancer patients: a phase I-II study," *Blood*; 84:1434-1441.
Gao et al. (2012) "Best: Improved Prediction of B-Cell Epitopes from Antigen Sequences," *PLoS One*; 7(6): e40104.
GenBank Accession No. M37897 "Mouse interleukin 10 mRNA, complete cds," dated Apr. 27, 1993.
GenBank Accession No. Np 000563 "interleukin-10 precursor [*Homo sapiens*]," dated Mar. 3, 1995.
Georgescu et al. (1997) "Interleukin-10 Promotes Activation-induced Cell Death of SLE Lymphocytes Mediated by Fas Ligand," *J. Clin. Invest.*; 100:2622-2633.
Gerstein et al. (2008) "Effects of Intensive Glucose Lowering in Type 2 Diabetes," *New England J of Medicine*; 358(24):2545-2559.
Gesser et al. (1997) "Identification of functional domains on human interleukin 10," *Proc. Natl. Acad. Sci.*; 94:14620-14625.
Gierens et al. (2000) "Interleukin-6 Stimulates LDL Receptor Gene Expression via Activation of Sterol-Responsive and Sp1 Binding Elements," *Arterioscler Thromb Vasc Biol.*; 20:1777-1783.
Gregoriadis et al., (2005) "Improving the therapeutic efficacy of peptides and proteins: a role for polysialic acids," *Int. J. Pharmaceutics*; 300(1-2):125-130.
Groux et al. (1998) "A transgenic model to analyze the immunoregulatory role of IL-10 secreted by antigen- presenting cells," *J Immunol*; 162:1723-1729.
Groux et al. (1998) "Inhibitory and stimulatory effects of IL-10 on human COB+ T cells," *J Immunol*; 160:3188-3193.
Hagenbaugh et al. (1997) "Altered immune responses in interleukin 10 transgenic mice," *J Exp Med*; 185:2101-2110.
Hamada et al. (2009) "Effect of Additives on Protein Aggregation," *Current Pharm Biotech*; 10:400-407.
Hashizume et al. (2010) "Overproduced interleukin 6 decreases blood lipid levels via upregulation of very-low-density lipoprotein receptor," *Ann Rheum Dis*; 69:741-746.
Heeschen et al. (2003) "Serum Level of the Antiinflammatory Cytokine Interleukin-1 0 Is an Important Prognostic Determinant in Patients With Acute Coronary Syndromes," *Circulation*; 107:2109-2114.
Hombach et al. (2013) "Arming Cytokine-induced Killer Cells With Chimeric Antigen Receptors: CD28 Outperforms Combined CD28-OX40 'Super-stimulation'," *Molecular Therapy*; 12:2268-2277.
Howard et al. (1993) "Interleukin 10 Protects Mice from Lethal Endotoxemia," *J. Exp. Med.*; 177:1205-1208.
Huang et al. (1996) "Interleukin 10 Suppresses Tumor Growth and Metastasis of Human Melanoma Cells: Potential Inhibition of Angiogenesis," Clinical Cancer Research, *The American Assn for Cancer Research*; 2(12):1969-1979.
Huang et al. (2010) "Depletion of Liver Kupffer Cells Prevents the Development of Diet-Induced Hepatic Steatosis and Insulin Resistance," 59:347-357.
Huntington et al. (2008) "IL-15 trans-presentation promotes human NK cell development and differentiation in vivo," *J. Exp. Med.*; 206:25-34.
Hustoft et al. (2012) "A Critical Review of Trypsin Digestion for LC-MS Based Proteomics," *InTech*; Chapter 4.
Infante et al. (2015) "A first-in-human dose escalation study of PEGylated recombinant human IL-10 (AM0010) in advanced solid tumors," *ASCO Meeting Abstracts*; 33(15 suppl):3017.
International Search Report; PCT/US01/42431, dtd. Aug. 20, 2002.
Ishikawa et al. (2005) "Interleukin-10 plasmid DNA inhibits liver and lung metastasis of Colon 26 adenocarcinoma in mice," *Proceedings of the Annual Meeting, American Association for Cancer Research*; vol. 46, Abstract # 3364.
Izbicki et al. (1997) "Prognostic value of immunohistochemically identifiable tumor cells in lymph nodes of patients with completely resected esophageal cancer," *New Engl J Med*; 337:1188-1194.

Jameson et al. (1994) "A rationally designed CD4 analogue inhibits experimental allergic encephalomyelitis," *Nature*; 368:744-746.
Jevševar et al. (2010) "PEGylation of therapeutic proteins," *Biotechnol. J.*; 5:113-128.
Jiang et al. (2015) "T-cell exhaustion in the tumor microenvironment," *Cell Death Dis*; 6:e1792.
Josephson et al. (2001) "Crystal Structure of the IL-10/1L-10R1 Complex Reveals A Shared Receptor Binding Site," *Immunity*; 14:35-46.
Jungbauer et al. (2007) "Current status of Technical protein refolding," *Journal of Biotechnology*; 128:587-596.
Katre (1993) "The Conjugation of Proteins with Polyethylene Glycol and Other Polymers Altering Properties of Proteins to Enhance their Therapeutic Potential," *Advanced Drug Delivery Reviews*; 10(1):91-114.
Khow and Suntrarachun (2012) "Strategies for production of active eukaryotic proteins in bacterial expression system," *Asian Pac. J. Biomed.*; 2(2):159-162.
Kimball et al (2002) "Clinical and Immunologic Assessment of Patients With Psoriasis in a Randomized, Double-blind, Placebo-Controlled Trial Using Recombinant Human Interleukin 10," *Arch Dermatol*; 138:1341-1346.
Kinstler et al. (1996) "Characterization and Stability of N-terminally PEGylated rhG-CSF," *Pharm. Res.*; 13:996-1002.
Kinstler et al. (2002) "Mono-N-terminal poly(ethylene glycol)-protein conjugates," *Advanced Drug Delivery Reviews*; 54:477-485.
Klompus et al. (2008) "A simple novel method for the preparation of noncovalent homodimeric, biologically active human interleukin 10 in *Escherichia coli*—Enhancing protein expression by degenerate PCR of 59 DNA in the open reading frame," *Protein Expression and Purification*; 62:199-205.
Kokura et al. (2003) "The blocking of NFkB activation by systemicinterleukin-10 gene therapy inhibits liver and lung metastasis of colon 26 adenocarcinoma in mice" *Gastroenterology*; 124(4): Abstract No. W965.
Kokura et al. (2005) "Interleukin-1 0 plasmid DNA inhibits subcutaneous tumor growth of Colon adenocarcinoma in mice," *Cancer Letters*; 218:171-179.
Kong et al. (2005) "In vivo activities of cytokine oncostatin M in the regulation of plasma lipid levels," *Journal of Lipid Research*; 46:1163-1171.
Körholz et al. (1997) "The Role of Interleukin-10 (IL-10) in IL-15—Mediated T-Cell Resnosas," Blood; 90(11):4513-4521.
Kundu et al. (1996) "Antimetastatic and antitumor activities of interleukin 10 in a murine model of breast cancer," *J Nail Cancer Inst*; 88:536-541.
Kundu et al. (1997) "Interleukin-10 inhibits tumor metastasis, down regulates MHC class I, enhances NK lysis," *Cellular Immunology*, Academic Press; 180(1):55-61.
Kute et al. (2012) "Understanding key assay parameters that affect measurements of trastuzumab-mediated ADCC against Her2 positive breast cancer cells," *Oncolmmunology*; 1(6):810-821.
Langowski et al. (2006) "IL-23 promotes tumour incidence and growth," *Nature*; 442:461-465.
Lasek et al. (2014) "Interleukin 12: still a promising candidate for tumor immunotherapy?" *Cancer lmmunol lmmunother*; 63:419-435.
Le et al. (2001) "Pre-existing tumor-sensitized T cells are essential for eradication of established tumors by IL-12 and cyclophosphamide plus IL-12," *J lmmunol*; 167:6765-6772.
Lehmann et al. (2014) "IL-12 Directs Further Maturation of Ex Vivo Differentiated NK Cells with Improved Therapeutic Potential," *PLoS One*; 9(1):e87131 (12 pages).
Lewington and Clark (2005) "Combined Effects of Systolic Blood Pressure and Total Cholesterol on Cardiovascular Disease Risk," *Circulation*; 112:3373-3374.
Lindhout et al. (2011) "Site-specific enzymatic polysialylation of therapeutic proteins using bacterial enzymes," *PNAS*; 108(18)7397-7402.
Liu et al. (2003) "IL-10 Mediates Suppression of the CD8 T Cell IFN- γ Response to a Novel Viral Epitope in a Primed Host," *J lmmunol*; 171:4765-4772.

(56) References Cited

OTHER PUBLICATIONS

Loebbermann et al. (2012) "IL-10 Regulates Viral Lung Immunopathology during Acute Respiratory Syncytial Virus Infection in Mice," *PLoS ONE*; 7(2):e32371.
Lopez et al. (2005) "IL-12 and IL-10 Expression Synergize to Induce the Immune-Mediated Eradication of Established Colon and Mammary Tumors and Lung Metastasis," *J Immunol*; 175:5885-5894.
Lowe et al. (1998) "Impact of Major Cardiovascular Disease Risk Factors, Particularly in Combination, on 22-Year Mortality in Women and Men," *Arch Intern Med*; 158:2007-2014.
Lu et al. (2004) "Prognostic factors in resected stage I non-small-cell lung cancer: a multivariate analysis of six molecular markers," *J Clin Oneal*; 22:4575-4583.
Lugli et al. (2010) "Transient and persistent effects of IL-15 on lymphocyte homeostasis in nonhuman primates," *Blood*; 116:3238-3248.
Lynch and Chapelle (2003) "Hereditary colorectal cancer," *New Eng I J Med*; 348:919-932.
Martin et al. (2001) "B-Cell Deficiency Suppresses Vaccine-Induced Protection against Murine Filariasis but Does Not Increase the Recovery Rate for Primary Infection," *Infect. Immun.*; 69(11):7067-7073.
Mattos et al. (2012) "PEGylation of interleukin-10 improves the pharmacokinetic profile and enhances the antifibrotic effectivity in CCI.—induced fibrogenesis in mice," *J Control Release*; 162(1):84-91.
Maus et al. (2014) "Antibody-modified T cells: CARs take the front seat for hematologic malignancies," *Blood*; 123(17):2625-2635.
Miki Toyokazu et al. (2000) "Anti-metastatic effect of IL-10 gene modification in human lung cancer cells is differentially regulated by organ microenvironments," *Proceedings of the Annual Meeting American Association for Cancer Research*; 41:3.
Monk (2011) "A Strategy for the Quantification of Protein Polyethylene Glycol (PEG) Derivatized Sites using iTRAQ," *University of California*, San Diego; 1-51.
Moore et al. (1990) "Homology of cytokine synthesis inhibitory factor (IL-10) to the Epstein-Barr virus gene BCRFI," *Science*; 248:1230-1234.
Moran et al. (1994) "Human leukemia inhibitory factor inhibits development of experimental atherosclerosis," *Arterioscler Thromb Vasc Biol.*; 14(8):1356-1363.
Motzer et al. (2001) "Randomized Multicenter Phase II Trial of Subcutaneous Recombinant Human Interleukin-12 Versus Interferon-α2a for Patients with Advanced Renal Cell Carcinoma," *Journal of Interferon and Cytokine Research*; 21:257-263.
Mumm et al. (2011) "IL-10 elicits IFNγ—dependent tumor immune surveillance," *Cancer Cell*; 20(6):781-796.
Naicker et al. (2009) "Interleukin-10 Promoter Polymorphisms Influence HIV-1 Susceptibility and Primary HIV-1 Pathogenesis," *J. Infect. Dis.*; 200(3):448-452.
Natsume et al. (2009) "Improving effector functions of antibodies for cancer treatment: Enhancing ADCC and CDC," *Drug Design, Development and Therapy*; 3:7-16.
Nenseter et al. (1992) "Role of liver endothelial and Kupffer cells in clearing low density lipoprotein from blood in hypercholesterolemic rabbits," *J of Lipid Res*; 33:867-877.
Neven et al. (2013) "A Mendelian predisposition to B cell lymphoma caused by IL-10R deficiency," *Blood*; 122(23):3712-3722.
Neyrinck et al. (2009) "Critical role of Kupffer cells in the management of diet-induced diabetes and obesity," *Biochemical and Biophysical Research Communications*; 385:351-356.
Nicholls et al. (2012) "Is niacin ineffective? or did AIM-HIGH miss its target?," *Cleveland Clinic Journ of Med*; 79(1):38-43.
Noguchi et al. (2003) "PDX-1 Protein Containing Its Own Antennapedia-Like Protein Transduction Domain Can Transduce Pancreatic Duct and Islet Cells," *Diabetes*; 52(7):1732-1737.
Osaki et al. (1999) "Potent antitumor effects mediated by local expression of the mature form of the interferon-γ inducing factor, interleukin-18 (IL-18)," *Gene Therapy*; 6:808-815.

Osborne (1998) "Tamoxifen in the treatment of breast cancer," *New Engl J Med*; 339:1609-1618.
Overdijk et al. (2011) "Epidermal Growth Factor Receptor (EGFR) Antibody-Induced Antibody-Dependent Cellular Cytotoxicity Plays a Prominent Role in Inhibiting Tumorigenesis, Even of Tumor Cells Insensitive to EGFR Signaling Inhibition," *Journal of Immunology*; 187:3383-3390.
Pardoll (2012) "The blockade of immune checkpoints in cancer immunotherapy," *Cancer*; 12:252-264.
Park et al. (2011) "IL-15-Induced IL-10 Increases the Cytolytic Activity of Human Natural Killer Cells," *Mol. Cells*; 32:265-272.
Pasut and Veronese (2012) "State of the art in PEGylation: The great versatility achieved after forty years of research," *Journal of Controlled Release*; 161:461-472.
Payne et al. (2010) "Product development issues for PEGylated proteins," *Pharmaceutical Development and Technology*; 16:423-440.
Pegram et al. (2012) "Interleukin 12: Stumbling Blocks and Stepping Stones to Effective Anti-Tumor Therapy," *Advancements in Tumor Immunotherapy and Cancer Vaccines*; Chapter 10:197-218.
Pellegrini et al. (2011) "IL-7 Engages Multiple Mechanisms to Overcome Chronic Viral Infection and Limit Organ Pathology," *Cell*; 144:1-13.
Pettit et al. (1997) "Structure-Function Studies of Interleukin 15 using Site-specific Mutagenesis, Polyethylene Glycol Conjugation, and Homology Modeling," *J. Biol. Chem.* 272:2312-2318.
Rachmawati et al. (2004) "Pharmacokinetic and Biodistribution Profile of Recombinant Human Interleukin-10 Following Intravenous Administration in Rats with Extensive Liver Fibrosis," *Pharm. Res.*; 21(11):2072-2078.
Rachmawati et al. (2007) "Chemical Modification of Interleukin-10 with Mannose 6-Phosphate Groups Yields a Liver-Selective Cytokine," *Drug Metabolism and Disposition*; 35(5):814-821.
Radwanski et al. (1998) "Pharmacokinetics and Leukocyte Responses of Recombinant Human Interleukin-10," *Pharm. Res.*; 15(12):1895-1901.
Ramirez-Montagut et al. (2003) "Immunity to melanoma: unraveling the relation of tumor immunity and autoimmunity," *Oncogene*; 22:3180-3187.
Re et al. (2002) "Preclinical evaluation of the antiproliferative potential of STI571 in Hodgkin's disease," *British Journal of Cancer*; 86:1333-1335.
Reynolds, et al. (2002) "Proteolytic 18O Labeling for Comparative Proteomics: Evaluation of Endoprotease Glu-C as the Catalytic Agent," *Journal of Proteome Research*; 1(1):27-33.
Roberts et al. (2012) "Chemistry for peptide and protein PEGylation," *Advanced Drug Delivery Reviews*; 64:116-127.
Rolfe et al. (2003) "Leukaemia inhibitory factor retards the progression of atherosclerosis," *Cardiovascular Research*; 58:222-230.
Russo et al. (2006) "Randomized trial of pegylated interferon a-2b monotherapy in haemodialysis patients with chronic hepatitis C," *Nephrol Dial Transplant*; 21:437-443.
Saha and Raghava (2006) "Prediction of continuous B-cell epitopes in an antigen using recurrent neural network," *Proteins*; 65:40-48.
Sakamoto et al. (2003) "Interleukin-10 gene therapy enhances antitumor effect of CPT-11 for lung metastasis of colon26 adenocarcinoma in mice," *Gastroenterology*; 124(4):A456-A457.
Sawaya et al. (2003) "Risk of cervical cancer associated with extending the interval between cervical-cancer screenings," *New Engl J Med*; 349:1501-1509.
Schäffner et al. (2001) "Cosecretion of Chaperones and Low-Molecular-Size Medium Additives Increases the Yield of Recombinant Disulfide-Bridged Proteins," *Applied and Environmental Microbiology*; 67(9):3994-4000.
Sela and Zisman (1997) "Different roles of D-amino acids in immune phenomena," *Faseb J.*; 11:449-456.
Shen et al. (2013) "Proprotein convertase subtilisin/kexin type 9 potentially influences cholesterol uptake in macrophages and reverse cholesterol transport," *FEBS Letters*; 587:1271-1274.
Smith et al. (1996) "Administration of interleukin-1 0 at the time of priming protects Corynebacterium parvum-primed mice against LPS- and TNF-alpha-induced lethality," *Cellular Immunology* 173(2):207-214.

(56) References Cited

OTHER PUBLICATIONS

Sneller et al. (2011) "IL-15 administered by continuous infusion to rhesus macaques induces massive expansion of CD8 T effector memory population in peripheral blood," *Blood*; 118(26):6845-6848.
Soman et al. (2009) "MTS dye based colorimetric CTLL-2 cell proliferation assay for product release and stability monitoring of Interleukin-15: Assay qualification, standardization and statistical analysis," *J Immunol Methods*; 348(1-2):83-94.
Song et al. (2012) "CD27 costimulation augments the survival and antitumor activity of redirected human T cells in vivo," *Blood*; 119(3):696-706.
Srivastava et al. (2013) "Effects of interleukin-18 on natural killer cells: costimulation of activation through Fc receptors for immunoglobulin," *Cancer Immunol Immunother*; 62(6):1073-1082.
Storici and Resnick (2006) "The delitto perfetto approach to in vivo site-directed mutagenesis and chromosome rearrangements with synthetic oligonucleotides in yeast," *Methods in Enzymology*; 409:329-345.
Sweredoski and Baldi (2009) "COBEpro: a novel system for predicting continuous B-cell epitopes," *Protein Eng Des Sel*; 22:113-120.
Syto et al. (1998) "Structural and biological stability of the human interleukin 10 homodimer," *Biochemistry*; 37(48):16943-16951.
Teng et al. (2015) "IL-12 and IL-23 cytokines: from discovery to targeted therapies for immune-mediated inflammatory diseases," *Nature Medicine*; 21:719-729.
Tilg et al. (2002) "Treatment of Crohn's disease with recombinant human interleukin 10 induces the proinflammatory cytokine interferon γ," *Gut*; 50:191-195.
Trandem et al. (2011) "Virally Expressed Interleukin-10 Ameliorates Acute Encephalomyelitis and Chronic Demyelination in Coronavirus-Infected Mice," *J. Virol.*; 85(14):6822-6831.
Tréhin et al. (2004) "Cellular uptake but low permeation of human calcitonin-derived cell penetrating peptides and Tat(47-57) through well-differentiated epithelial models," *Pharm. Research*; 21:1248-1256.
Tsumoto et al. (2003) "Practical considerations in refolding proteins from inclusion bodies," *Protein Expression and Purification*; 28:1-8.
Tsumoto et al. (2004) "Role of Arginine in Protein Refolding, Solubilization, and Purification," *Biotechnol. Prog.*; 20:1301-1308.
Valabrega et al. (2007) "Trastuzumab: mechanism of action, resistance and future perspectives in HER2-overexpressing breast cancer," *Annals of Oncology*; 18:977-984.
Van Deventer et al. (1997) "Multiple Doses of Intravenous Interleukin 10 in Steroid-Refractory Crohn's Disease," *Gastroenterology*, 113:383-389.
Vicari and Trinchieri (2004) "Interleukin-10 in viral diseases and cancer: exiting the labyrinth?," *Immunological Reviews*; 202:223-236.
Vigneron et al. (2013) "Database of T cell-defined human tumor antigens: the 2013 update," *Cancer Immunity*; 13:15-20.
Virgin, et al. (2009) "Redefining Chronic Viral Infection," *Cell*; 138:30-50.
Von Andrian and Mackay (2000) "T-cell function and migration. Two sides of the same coin," *New Engl J Med*; 343:1020-1034.
Waldmann et al. (2011) "Safety (toxicity), pharmacokinetics, immunogenicity, and impact on elements of the normal immune system of recombinant human IL-15 in rhesus macaques," *Blood*; 117:4787-4795.
Walter and Nagabhushan (1995) "Crystal structure of interleukin 10 reveals an interferon gamma-like fold," *Biochemistry*; (38):12118-12125.
Wee et al. (2010) "SVM-based prediction of linear B-cell epitopes using Bayes Feature Extraction," *BMC Genomics*; 11(Su pp. 4):521.
Wender et al. (2000) "The design, synthesis, and evaluation of molecules that enable or enhance cellular uptake: peptoid molecular transporters," *Proc. Natl. Acad. Sci. USA*; 97:13003-13008.

Wilson et al. (2011) "The role of IL-10 in regulating immunity to persistent viral infections," *Curr Top Microbiol Immunol.*; 350:39-65.
Witsch et al. (2010) "Roles for Growth Facotes in Cancer Progression," *Physiology*; 25(2):85-101.
Wu et al. (2012) "Immunotherapies: The Blockade of Inhibitory Signals," *Int. J. Biol. Sci.*; 8:1420-1430.
Xu et al. (2010) "Regulation of Antitumor Immune Responses by the IL-12 Family Cytokines, IL-12, IL-23, and IL-27," *Clinical and Developmental Immunology*; Article ID:832454 (9 pages).
Yamaguchi and Miyazaki (2014) "Refolding Techniques for Recovering Biologically Active Recombinant Proteins from Inclusion Bodies," *Biomolecules*; 4:235-251.
Yoshioka et al. (2011) "Development of a novel DDS for site-specific PEGylated proteins," *Chem. Central J.*; 5:25.
Younes et al. (2004) "Phase II Clinical Trial of Interleukin-12 in Patients with Relapsed and Refractory Non-Hodgkin's Lymphoma and Hodgkin's Disease," *Clinical Cancer Research*; 10:5432-5438.
Zauner et al. (1996) "Glycerol Enhancement of Ligand-Polylysine/DNA Transfection," *Bio Techniques*; 20:905-913.
Zdanov et al. (1995) "Crystal structure of interleukin-10 reveals the functional dimer with an unexpected topological similarity to interferon γ," *Structure*; 3:591-601.
Zdanov et al. (1996) "Crystal structure of human interleukin-10 at 1.6 A resolution and a model of a complex with its soluble receptor," *Protein Sci.*; (10):1955-1962.
Zender et al. (2002) "VP22-mediated intercellular transport of p53 in hepatoma cells in vitro and in vivo," *Cancer Gene Ther.*; 9(6):489-496.
Zheng et al. (1996) "Interleukin-10 inhibits tumor metastasis through an NK cell-dependent mechanism," *J Exp Med*; 184:579-584.
Muecke, Susanne, et al., (2000) "Suppression of the Tumorigenic Growth of Burkitt'S Lymphoma in Immunodeficient Mice by Cytokine Gene Transfer Using EBV-Derived Episomal Expression Vectors", Int. J. Cancer, 86:301-306.
Mumm, John B., et al., (2012) "Killing from within" OncoImmunology, 1(9):1598-1600.
Klebanoff, CA et al., (2004) "IL-15 Enhances the in vivo Antitumor Activity of Tumor-reactive CD8+ T Cells", Proceedings of the National Academy of the Sciences of the U.S.A., 101(7):1969-1974.
Steel, JC et al., (2012) "Biology and its Therapeutic Implications in Cancer", Trends in Pharmacological Sciences, 33(1):35-41.
Chang, et al., (2017) "CARs: Synthetic immunoreceptors for cancer therapy and beyond", Trends Mol. Med., 23:430-450.
Hermanson, et al., (2015) "Utilizing chimeric antigen receptors to direct natural killer cell activity", Frontiers in Immunology, 6:195.
Jaspers, et al., (2017) "Development of CART cells designed to improve antitumor efficacy and safety", Pharmac. & Therap., http://dx.doi.org,/1 0.1 016/j.pharmthera.2017.03.012.
Jensen, et al., (2015) "Designing chimeric antigen receptors to effectively and safely target tumors", Curr. Opin. Immunol., 33:9-15.
Chmielewski, et al, (2015) "TRUCKs: the fourth generation of CARs", Exp. Opin. Bioi. Ther., 15:1145-1154.
Hombach, et al., (2012) "OX40 costimulation by a chimeric antigen receptor abrogates CD28 and IL-2 induced IL-10 secretion by redirected CD4+ T cells", OncoImmunol., 1:458-466.
Newick, et al., (2016) "CART cell therapy for solid tumors", Annu. Rev. Med., 68:139-152.
Gill, et al., (2015) "Going Viral: chimeric antigen receptor T-cell therapy for hematological malignancies", Immunol. Rev., 263:68-89.
Aukrust et al., (2005) "Potential role for immunomodulatory therapy in atherosclerotic plaque stabilization", Expert Opinion Pharmacother, 6:2169-2180.
Cheon, H.G. (2013) "Latest research and development trends in non insulin anti-diabetics", Arch. Pharm. Res., 36:145-153.
Fichtlscherer et al., (2004) "Interleukin-10 serum levels and systemic endothelial vasoreactivity in patients with aoronary artery desease", J. Am. Coll. Cardiol., 44:44-49.

(56) References Cited

OTHER PUBLICATIONS

Bowie, James, U., et al. (1990) "Deciphering the Message in Protein Sequences: Tolerance to Amino Acid Substitutions", Science, 247:1306-1310.

Burgess, Wilson, H., et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Bioi., 111:2129-2138.

Bork, Peer, (2000) "Powers and Pitfalls in Sequence Analysis: The 70% Hurdle", Genome Research, 10:398-400.

Lazar, Eliane, et al. (1988) "Transforming Growth Factor alpha: Mutation of Aspartic Acid 47 and Leucine 48 Results n Different Biological Activities", Mol. Cell. Bioi., 8:1247-1252.

UniProt reference A2T676 (1L 1 O_PANTR) (downloaded from http://www.uniprot.org/uniprot!A2T6Z6, last sequence update Mar. 6, 2007).

UniProt reference P79338 (1L 1 O_MACFA) (downloaded from http://www.uniprot.org/uniprot/P79338, last sequence update May 1, 1997).

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Dec. 11, 2013, 3 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 31, 2014, 3 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jul. 17, 2014, 6 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Mar. 24, 2015, 7 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 12, 2016, 7 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Oct. 2, 2016, 7 pages.

NCT02923921, "Randomized Study of AM0010 in Combination With FOLFOX Compared to FOLFOX Alone as Secondline Tx in Pts With Meta Pancreatic Cancer That Has Progressed During or Following a FirstLine Gemcitabine containing Regimen", ClinicalTrials.gov, Oct. 4, 2016, 3 pages.

\* cited by examiner

FIG. 1A

Complete Human IL-10 (NP_000563)
MHSSALLCCLVLLTGVRASPGQGTQSENSCTHFPGNLPNMLRDLRDAFSRVKTFFQMK
DQLDNLLLKESLLEDFKGYLGCQALSEMIQFYLEEVMPQAENQDPDIKAHVNSLGENLK
TLRLRLRRCHRFLPCENKSKAVEQVKNAFNKLQEKGIYKAMSEFDIFINYIEAYMTMKI
RN

FIG. 1B

Mature Human IL-10 (BC104252)
SPGQGTQSENSCTHFPGNLPNMLRDLRDAFSRVKTFFQMKDQLDNLLLKESLLEDFKGY
LGCQALSEMIQFYLEEVMPQAENQDPDIKAHVNSLGENLKTLRLRLRRCHRFLPCENKS
KAVEQVKNAFNKLQEKGIYKAMSEFDIFINYIEAYMTMKIRN

Endoproteinase GluC Protein Sequence:

```
  1  VILPNNDRHQITDTTNGHYAPVTYIQVEAPTGTFIASGVVVGKDTLLTNKHVVDATHGDP
 61  HALKAFPSAINQDNYPNGGFTAEQITKYSGEGDLAIVKFSPNEQNKHIGEVVKPATMSNN
121  AETQVNQNITVTGYPGDKPVATMWESKGKITYLKGEAMQYDLSTTGGNSGSPVFNEKNEV
181  IGIHWGGVPNEFNGAVFINENVRNFLKQNIEDIHFANDDQPNNPDNPNNPDNPNNPD
241  EPNNPDNPNNPDNPDNGDNNNSDNPDAAHHHHHH
```

FIG. 2

METHOD FOR ASSESSING PROTEIN IDENTITY AND STABILITY

CROSS-REFERENCE TO RELATED APPLICATION

This application claims priority benefit of U.S. provisional application Ser. No. 61/836,034, filed Jun. 17, 2013, which application is incorporated herein in its entirety.

FIELD OF THE INVENTION

The present invention relates to, among other things, methods of assessing the identity and stability of compositions comprising pegylated interleukin-10 and other pegylated interleukin-10—related molecules.

INTRODUCTION

The cytokine interleukin-10 (IL-10) is a pleiotropic cytokine that regulates multiple immune responses through actions on T cells, B cells, macrophages, and antigen presenting cells. IL-10 may suppress immune responses by inhibiting expression of IL-1α, IL-1β, IL-6, IL-8, TNF-α, GM-CSF and G-CSF in activated monocytes and activated macrophages, and it also suppresses IFN-γ production by natural killer cells. Although IL-10 is predominantly expressed in macrophages, expression has also been detected in activated T cells, B cells, mast cells, and monocytes. In addition to suppressing immune responses, IL-10 exhibits immuno-stimulatory properties, including stimulating the proliferation of IL-2—and IL-4—treated thymocytes, enhancing the viability of B cells, and stimulating the expression of MHC class II.

As a result of its pleiotropic activity, IL-10 has been linked to a broad range of diseases, disorders and conditions, including inflammatory conditions, immune-related disorders, fibrotic disorders and cancer. Clinical and pre-clinical evaluations with IL-10 for a number of such diseases, disorders and conditions have solidified its therapeutic potential. Moreover, pegylated IL-10 has been shown to be more efficacious than non-pegylated IL-10 in certain therapeutic settings.

In view of the prevalence and severity of IL-10—associated diseases, disorders and conditions, IL-10—related agents that modulate aspects of IL-10 function have tremendous therapeutic value. As such, accurate and reproducible methods for confirming the identity and stability, among other characteristics, of an IL-10—related therapeutic agent prior to administration to a subject are of great interest.

SUMMARY

The present disclosure is drawn, in part, to methods and other technologies that may be used to determine whether compositions (e.g., pharmaceutical compositions) comprising pegylated IL-10 meet particular product-related specifications prior to being administered to a subject for the treatment and/or prevention of the diseases, disorders and conditions, and/or the symptoms thereof, described herein.

The terms "IL-10", "IL-10 polypeptide(s)," "IL-10-agent(s)", and "IL-10 molecule(s)" are used interchangeably herein and include human and non-human IL-10—related polypeptides, including homologs, variants (including muteins), and fragments thereof, as well as IL-10 polypeptides having, for example, a leader sequence (e.g., a signal peptide). Unless otherwise indicated, the aforementioned terms also encompass pegylated versions of IL-10, wherein the PEG moiety has a molecular weight within the ranges described herein. As used hereafter, the terms "PEG-IL-10" and "pegylated interleukin-10" refer to an IL-10 dimeric molecule wherein one or both monomers are pegylated and wherein each PEG moiety is approximately ≥5 kDa. In particular embodiments, the IL-10 molecule is pegylated at the N-terminus of one or both monomers and each PEG moiety is about 5 kDa to about 20 kDa.

Because biologic agents are sensitive to changes in the starting materials and manufacturing processes used in their production, they may be difficult to consistently generate and characterize. Indeed, the production of biologics requires very rigorous quality control due to the potential for undesirable protein modifications and the possibilities for contamination of the biologic product. As a result, the integrity of the amino acid sequence of a protein biologic has to be confirmed for each production batch in order to ensure that it possesses, among other characteristics, the requisite amino acid identity (e.g., amino acid sequence). This is generally effected through the use of a lot release assessment (e.g., a lot release assay). Confirmation of amino acid identity through the use of a lot release assay generally provides an indication that the biologic possesses the required purity, potency, etc.

In order to be useful, data generated by a lot release assay must be consistent and reproducible, including scenarios where an individual performs the release assay using different equipment for separate batches; a different individual performs the release assay using the same equipment as the first individual; and a different individual performs the release assay using different equipment than the first individual. The methodology must provide consistent results wherein the nature of the molecule being tested does not interfere with the intrinsic mechanism by which the analytical method generates data. Thus, in the case of pegylated molecules, the site(s) of pegylation require rigorous testing to determine whether the release methodology is capable of eliciting meaningful data.

Peptide mapping is a powerful method frequently employed in the lot release assessment process. It provides for the determination of the primary amino acid sequence of a molecule, and thus is an indication of its identity. Peptide mapping is an indispensable analytical method for quality control of recombinantly-derived proteins, including protein biologics. A peptide map is essentially a "fingerprint" of a protein resulting from several chemical processes that provide a comprehensive understanding of the protein being analyzed. Peptide mapping involves fragmentation of the protein by enzymatic digestion or chemical cleavage, with subsequent separation and analysis of the fragments.

In order to be used effectively and safely in the treatment and/or prevention of IL-10—related diseases, disorders and conditions, and/or the symptoms thereof, pharmaceutical compositions comprising the PEG-IL-10 molecules contemplated herein should possess defined specifications (e.g., maintenance of the stability of the pharmaceutical composition for the entirety of its shelf-life), as determined, in large part, by the integrity of the primary amino acid sequence over time. In addition, the location of the pegylation modification(s) can be determined by a specific peptide fragment signature. In one embodiment, the present disclosure relates to methods and other technologies useful for reproducibly determining whether particular batches ("lots") of pharmaceutical compositions comprising PEG-IL-10 meet the required specifications (e.g., maintenance of the primary amino acid sequence and site of pegylation) for bulk drug substance (BDS) and final drug product (DP).

The present disclosure contemplates a method of confirming the integrity of a pegylated protein, comprising providing a sample comprising the pegylated protein, fragmenting the pegylated protein to yield a test plurality of peptides, and comparing the test plurality of peptides to a reference standard (by, e.g., by use of a computer); wherein the integrity of the pegylated protein is confirmed by demonstrating equivalency of the test plurality of peptides and the reference standard.

According to the present disclosure, the term "integrity", as used in the context of a pegylated protein, refers to a characteristic that, if present in one pegylated protein (e.g., a test pegylated protein), indicates that the pegylated protein is equivalent to another pegylated protein (e.g., a reference pegylated protein). In particular embodiments, the characteristic is the amino acid sequence of a pegylated protein. Thus, using the methods described herein, one of ordinary skill in the art is able to determine whether the amino acid sequence of one pegylated protein is equivalent to that of another pegylated protein.

In certain embodiments, the reference standard comprises a plurality of reference peptides generated from fragmenting a reference protein or a reference pegylated protein. The pegylated protein is the same as the reference pegylated protein in particular embodiments.

The present disclosure contemplates embodiments wherein the fragmenting is carried out by contacting the pegylated protein with a proteolytic agent such as a peptidase. The peptidase may be, for example, trypsin or glutamyl endopeptidase (Endo Glu-C).

In particular embodiments, the aforementioned peptide members of the test plurality of peptides are separated by chromatography or electrophoresis. Certain embodiments contemplate determining the absolute mass of each member of the test plurality of peptides by mass spectrometry. Methods of mass spectrometry include, but are not limited to, ESI-MS, ESI-MS/MS, ESI-TOF MS, MALDI MS and MALDI-TOF MS. The absolute mass of each member of the reference plurality of proteins is frequently stored in electronic media such as a database.

Embodiments of the present disclosure pertain to methods of confirming the identity of a plurality of peptides generated by an Endo Glu-C digestion of a pegylated human interleukin-10 by comparing the plurality of peptides to a PEG-hIL-10 reference standard, wherein the identity of the plurality of peptides is confirmed by demonstrating equivalency to the reference standard. The reference standard may comprise a plurality of reference peptides corresponding to those generated from digesting a reference hPEG-IL-10 or a reference hIL-10.

In the context of the present disclosure, equivalency of one group of peptides (e.g., a test plurality of peptides) to another group of peptides (e.g., a reference plurality of peptides) can be determined using any art-accepted method. By way of example, but not limitation, mass spectrometry can be used in evaluating whether the peptides resulting from enzymatic digestion of a protein yield the expected peptide mass fingerprint. Equivalency parameters may be established by a regulatory authority (e.g., FDA or foreign equivalent) to ensure that a peptide biologic meets particular requirements and thus is safe and effective for it intended purpose.

The present disclosure also provides methods of confirming the integrity (e.g., amino acid sequence) of a pegylated interleukin-10, comprising providing a sample comprising a test PEG-IL-10, fragmenting the test PEG-IL-10 (e.g, PEG-hIL-10) to yield a test plurality of peptides, and comparing (e.g., by use of a computer) the test plurality of peptides to a reference standard; wherein the integrity of the pegylated interleukin-10 is confirmed by demonstrating equivalency of the test plurality of peptides and the reference standard. The reference standard may encompass a plurality of reference peptides generated from fragmenting a reference PEG-IL-10 or a reference IL-10. In particular embodiments, the test PEG-IL-10 is the same as the reference PEG-IL-10.

In certain embodiments of the present disclosure, the fragmenting is carried out by contacting the test PEG-IL-10 with a proteolytic agent. The proteolytic agent may be a peptidase, such as trypsin or Endo Glu-C. Fragmenting of the test PEG-IL-10 with Endo Glu-C results in more discrete peptide fragments than fragmenting the test PEG-IL-10 with trypsin. In this context, the term "discrete" indicates that there is a defined, reproducible fingerprint. That is, digestion with Endo Glu-C results in a distinct pattern of resolvable peaks. In contrast, digestion with trypsin results in multiple overlapping, non-resolvable peaks.

In particular embodiments, the peptide members of the test plurality of peptides are separated by chromatography, whereas they are separated by electrophoresis in other embodiments. The absolute mass of each member of the test plurality of peptides may be determined by mass spectrometry, including the following technologies: ESI-MS, ESI-MS/MS, ESI-TOF MS, MALDI MS and MALDI-TOF MS. In regards to the reference plurality of peptides, the absolute mass of each member may be determined by mass spectrometry. Data regarding the absolute mass of each member of the reference plurality of peptides may be stored in a computer database or other electronic media.

In some embodiments, the reference peptides generated from fragmentation of the reference PEG-IL-10 are approximately equivalent to the reference peptides generated from fragmentation of the reference IL-10, as determined by, for example, ESI-MS, ESI-MS/MS, ESI-TOF MS, MALDI MS or MALDI-TOF MS. In the present disclosure, the meaning of "approximately" and similar terms derives from the context in which they are used. For example, the statement that "the reference peptides generated from digestion of the reference PEG-hIL-10 are approximately equivalent to the reference peptides generated from digestion of the reference hIL-10" indicates that the majority of peptides resulting from both digestions are the same, but that there may be some differences (nominal for the most part) as would be expected when pegylated proteins are involved.

In still further embodiments, the present disclosure contemplates methods of confirming the amino acid sequence of a pegylated human interleukin-10 by providing a sample comprising a test PEG-hIL-10, digesting the test hPEG-IL-10 with Endo Glu-C to yield a test plurality of peptides, and comparing (by, e.g., an algorithm or some type of computerized system) the test plurality of peptides to a reference standard; wherein the amino acid sequence of the pegylated human interleukin-10 is confirmed by demonstrating equivalency of the test plurality of peptides and the reference standard. In such methods, the reference standard may be a plurality of reference peptides generated from digesting a reference hPEG-IL-10 or a reference hIL-10. The test PEG-hIL-10 and the PEG-hIL-10 are the same as in particular embodiments. As previously mentioned, digesting the test PEG-hIL-10 with Endo Glu-C results in more discrete peptide fragments than digesting the test PEG-hIL-10 with trypsin.

In some embodiments, the pegylated IL-10 polypeptides described herein comprise at least one PEG molecule covalently attached to at least one amino acid residue of at least one monomer of IL-10. Such pegylated polypeptides may comprise a mixture of mono-pegylated and di-pegylated IL-10 monomers. References herein to "mono-pegylated" or "di-pegylated", or equivalents thereof, are meant to be construed more broadly than to just mono-pegylated and di-pegylated IL-10. To illustrate, two or more different sites on each IL-10 monomer might be modified by introducing more than one mutation to the IL-10 amino acid sequence and then pegylating each of them, or one site on each IL-10 monomer may be pegylated in combination with pegylation of the N-terminus. Exemplary pegylation conditions are described herein. The PEG component may be any PEG tolerated by the peptides. By way of example, the PEG component of the modified peptide may have a molecular mass from 5 kDa to 20 kDa in some embodiments, a molecular mass greater than 20 kDa in other embodiments, or a molecular mass of at least 30 kDa in still other embodiments. PEGs having other molecular mass values are also contemplated and are described herein.

In particular embodiments, the present disclosure contemplates pegylated polypeptides having a bioactivity approximating the bioactivity of SEQ ID NO:2. Bioactivity may be determined by any method known in the art, including a chemokine release assay or an MC/9 cell proliferation assay. Exemplary protocols for such assays are described herein.

The present disclosure includes pharmaceutical compositions comprising the IL-10 molecules described herein, and a pharmaceutically acceptable diluent, carrier or excipient. In some embodiments, the excipient is an isotonic injection solution. The pharmaceutical compositions may be suitable for administration to a subject (e.g., a human), and may comprise one or more additional prophylactic or therapeutic agents. In certain embodiments, the pharmaceutical compositions are contained in a sterile container (e.g., a single- or multi-use vial or a syringe). A kit may contain the sterile container(s), and the kit may also contain one or more additional sterile containers comprising at least one additional prophylactic or therapeutic agent or any other agent that may be used in pharmacological therapy.

Additional embodiments of the present disclosure comprise a method of treating or preventing a disease, disorder or condition in a subject (e.g., a human), comprising administering a therapeutically effective amount of an IL-10 molecule described herein. In various embodiments of the present disclosure, the disease, disorder or condition is a proliferative disorder, including a cancer (e.g., a solid tumor or a hematological disorder); an immune or inflammatory disorder, including inflammatory bowel disease, psoriasis, rheumatoid arthritis, multiple sclerosis, and Alzheimer's disease; thrombosis or a thrombotic condition or disorder, including a state of hypercoagulation; a fibrotic disorder; a viral disorder, including, but not limited to, human immunodeficiency virus, hepatitis B virus, hepatitis C virus and cytomegalovirus; a cardiovascular disorder, including atherosclerosis or other cardiovascular-related disorders wherein the subject may have elevated cholesterol and/or other abnormal metabolic-related parameters (e.g., abnormal blood glucose levels, insulin levels, or lipid levels).

In the methods of treating or preventing a disease, disorder or condition, administration of the therapeutically effective amount of a polypeptide described herein may be by any route appropriate for the polypeptide, including parenteral injection (e.g., subcutaneously). One or more additional prophylactic or therapeutic agents may be administered with (e.g., prior to, simultaneously with, or subsequent to) the peptide, and/or it may be administered separate from or combined with the peptide.

BRIEF DESCRIPTION OF THE DRAWINGS

FIG. 1A depicts the complete 178 amino acid human IL-10 sequence. (SEQ ID NO:1): The 18 amino acid signal peptide is underlined.

FIG. 1B depicts the 160 amino acid mature human IL-10 sequence. (SEQ ID NO:2):

FIG. 2 depicts the Endo Glu-C amino acid sequence (SEQ ID NO:3).

DETAILED DESCRIPTION

Figure 3A:
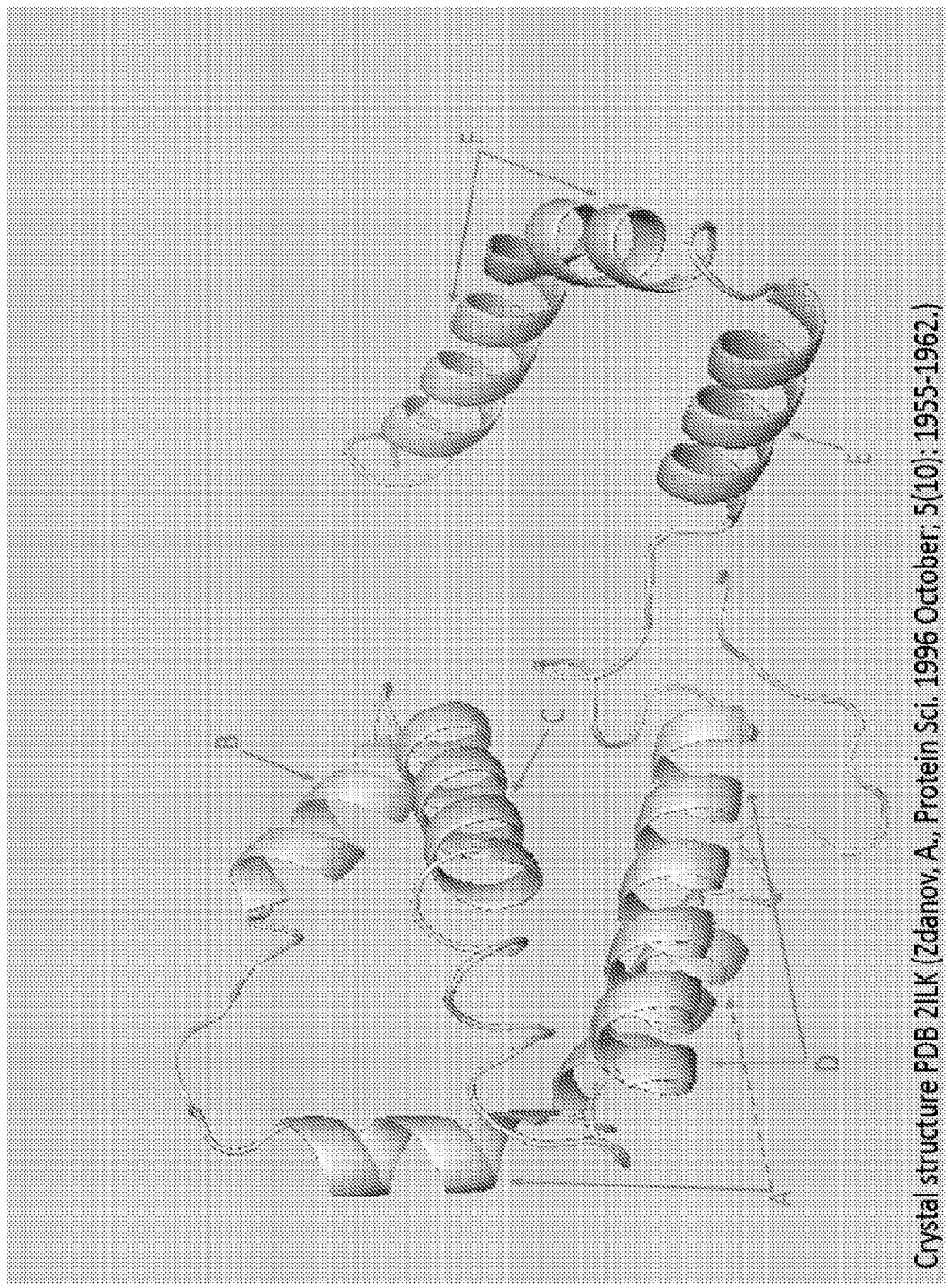
FIG. 3A is a protein crystal structure ribbon representation (top view) of the human IL-10 monomer. The six helices are labeled A-F.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of the smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

The production of biologics requires very rigorous quality control due to the potential for undesirable protein modifications and the numerous possibilities for contamination of the biologic product. A lot release assay is generally used to assess and ensure, for example, the integrity of the amino acid sequence of the active pharmaceutical ingredient (API) for each production batch ("lot").

The present disclosure relates generally to pegylated IL-10 molecules, including PEG-IL-10. In particular embodiments, the present disclosure is drawn to methods and other technologies, including lot release assessments, useful in determining whether compositions (e.g., pharmaceutical compositions) comprising PEG-IL-10 molecules meet particular product-related specifications before they are administered to a subject for the treatment and/or prevention of various IL-10—related diseases, disorders and conditions, and/or the symptoms thereof. In certain embodiments, the PEG-IL-10 molecules and compositions (e.g., pharmaceutical compositions) thereof, are used to treat and/or prevent inflammatory- and immune-related disorders; thrombotic disorders, fibrotic disorders, cancer and cancer-related disorders; and cardiovascular disorders (e.g., atherosclerosis). In particular embodiments, the PEG-IL-10 molecules and compositions (e.g., pharmaceutical compositions) thereof, are used to treat and/or prevent cholesterol-related disorders, including hypercholesterolemia.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10), a nucleic acid (e.g., a nucleic acid encoding native human IL-10); a pharmaceutical composition comprising the foregoing, or a diagnostic agent, to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering PEG-IL-10 or a pharmaceutical composition comprising PEG-IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering PEG-IL-10 or a pharmaceutical composition comprising PEG-IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, peptide, polypeptide, membrane-associated or membrane-bound molecule, or complex thereof, that can act as an agonist or antagonist of a receptor. "Ligand" encompasses natural and synthetic ligands, e.g., cytokines, cytokine variants, analogs, muteins, and binding compositions derived from antibodies. "Ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. Moreover, the term includes a membrane-bound ligand that has been changed, e.g., by chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an IL-10 molecule (or the nucleic acid molecules encoding them), either directly or indirectly; or to enhance the ability of a molecule to produce an effect comparable to that of an IL-10 molecule. The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator may act alone, or it may use a cofactor, e.g., a protein, metal ion, or small molecule. The term "modulator" includes agents that operate through the same mechanism of action as IL-10 (i.e., agents that modulate the same signaling pathway as IL-10 in a manner analogous thereto) and are capable of eliciting a biological response comparable to (or greater than) that of IL-10.

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term may also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity. As previously indicated, the skilled artisan recognizes that use of different methodologies may result in IL-10 that is more or less active—either in apparent activity due to differences in calculating protein concentration or in actual activity—than a hIL-10 reference standard. The skilled artisan will be able to factor in these differences in determining the relative bioactivities of an IL-10 molecule (e.g., PEG-IL-10) versus hIL-10.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes. Unless otherwise indicated, use of terms such as "mutant of IL-10" refer to IL-10 muteins.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates IL-10—related polypeptides and corresponding nucleic acid molecules from other species.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein in reference to native human IL-10 or an IL-10 mutein, the terms "modified", "modification" and the like refer to one or more changes that enhance a desired property of human IL-10 or an IL-10 mutein. Such desired properties include, for example, prolonging the circulation half-life, increasing the stability, reducing the clearance, altering the immunogenicity or allergenicity, and enabling the raising of particular antibodies (e.g., by introduction of unique epitopes) for use in detection assays. As discussed in detail hereafter, modifications to human IL-10 or an IL-10 mutein that may be carried out include, but are not limited to, pegylation (covalent attachment of one or more molecules of polyethylene glycol (PEG), or derivatives thereof); glycosylation (e.g., N-glycosylation), polysialylation and hesylation; albumin fusion; albumin binding through, for example, a conjugated fatty acid chain (acylation); Fc-fusion; and fusion with a PEG mimetic.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant methods.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make upgreater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The terms "post-translational modification" and "PTM" refer to steps in protein biosynthesis whereby the polypeptides resulting from ribosomal translation undergo modifications (e.g., folding and cleavage) before becoming the mature protein product. After translation, PTM of amino acids generally extends the range of functions of the protein by attaching it to other biochemical functional groups (e.g., acetate, phosphate, and various lipids and carbohydrates), thereby changing the chemical nature of the amino acids or making structural changes thereto (e.g., formation of disulfide bonds). Modifications such as phosphorylation are involved in controlling the behavior of a protein, including the activation or inactivation of an enzyme. Additional examples of PTMs pertain to enzymatic cleavage of the protein (e.g., removal of a propeptide) or cleavage of the methionine residue with which most nascent polypeptides begin. PTMs are frequently detected by mass spectrometry.

As used herein, the term "lot release" generally refers to the biologic-specific standard(s) that must be present before a biologic agent may be administered to a subject, and the term "lot release assay" generally refers to a bioassay which, for example, a regulatory authority has concluded accurately and reproducibly indicates whether the biologic-specific standard(s) have been met. The degree of regulatory oversight to which a biologic is subjected during lot release is associated with its indication and risk/benefit assessment, and considerations include the following: age of the target subject population; disease state being treated (e.g., life threatening, acute, or chronic); anticipated duration of treatment; general health status of the subject population; objective of therapy (e.g., treatment, prevention or diagnosis); and the size of the subject population.

IL-10 and Pegylated IL-10

The anti-inflammatory cytokine IL-10, also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-$\alpha$, -$\beta$, -$\gamma$, -$\delta$, -$\epsilon$, -$\kappa$, -$\Omega$, and -$\tau$) and interferon-like molecules (limitin, IL-28A, IL-28B, and IL-29).

IL-10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFN-$\gamma$, IL-2, IL-3, TNF$\alpha$ and GM-CSF, IL-10 is also stimulatory towards certain T cells and mast cells and stimulates B-cell maturation, proliferation and antibody production. IL-10 can block NF-$\kappa$B activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

Human IL-10 is a homodimer with a molecular mass of 37 kDa, wherein each 18.5 kDa monomer comprises 178 amino acids, the first 18 of which comprise a signal peptide, and two pairs of cysteine residues that form two intramolecular disulfide bonds. Each monomer of mature hIL-10 comprises 160 amino acid residues. The IL-10 dimer becomes biologically inactive upon disruption of the non-covalent interactions between the two monomer subunits. FIG. 1A depicts the complete 178 amino acid human IL-10 sequence (the 18 amino acid signal peptide is underlined), and FIG. 1B depicts the 160 amino acid mature human IL-10 sequence.

The present disclosure contemplates human IL-10 and murine IL-10, which exhibit 80% homology, and use thereof. In addition, the scope of the present disclosure includes IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

Figure 3B:
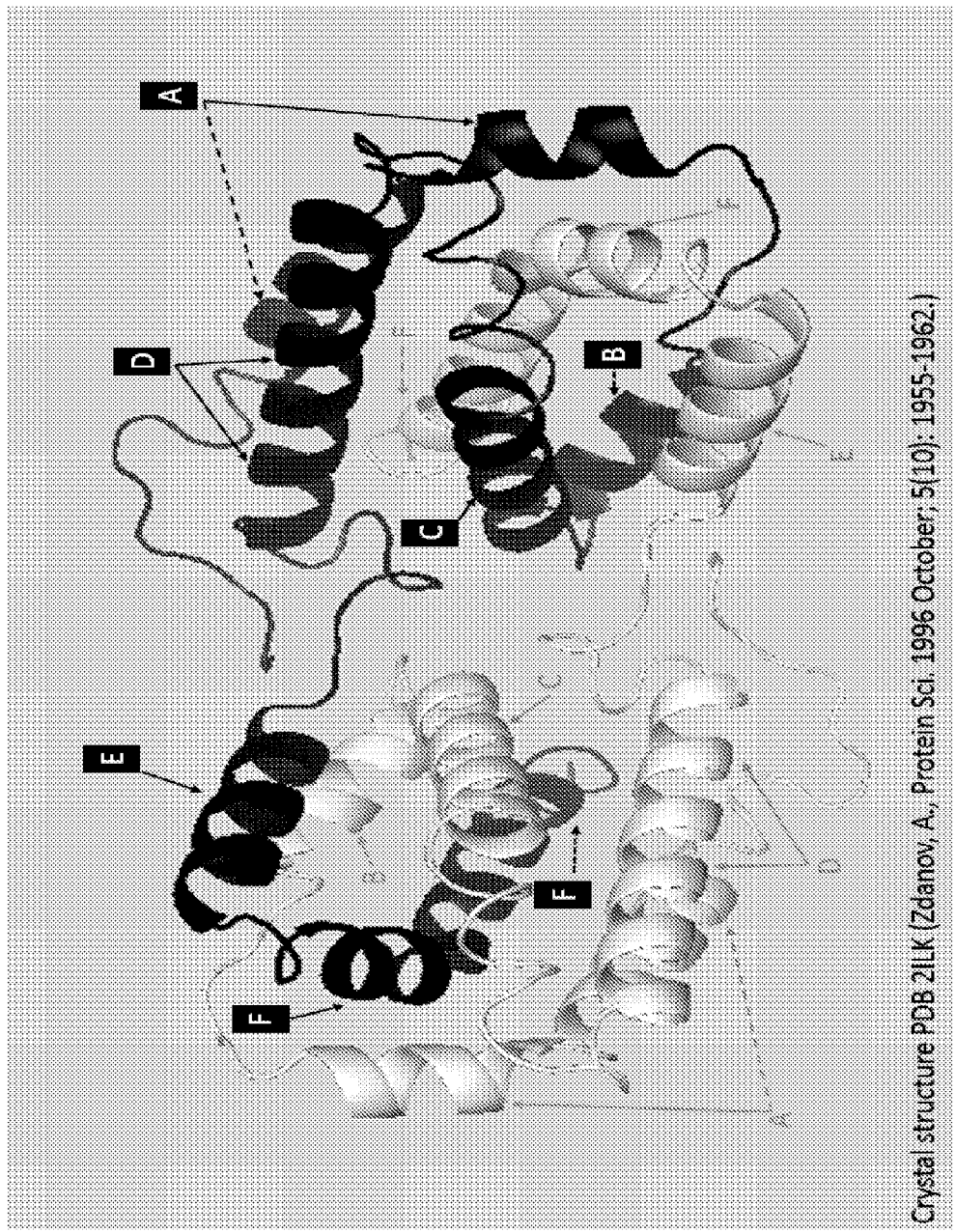
FIG. 3B is a protein crystal structure ribbon representation (top view) of the human IL-10 homodimer. One monomer is gray and the other monomer is black. The six helices are labeled A-F.

Crystallographic data from a number of sources, including data obtained from the crystal structure of IL-10 (Zdanov, A. et al, (1995) Structure (Lond) 3:591-601 and Walter, M. and Nagabhushan, T., (1995) Biochemistry (38): 12118-25); and a model of the crystal structure of hIL-10 with its soluble receptor (Zdanov, A. et al., (1996) Protein Sci. (10):1955-62) have been published. Each 160 amino acid monomer of mature human IL-10 (hIL-10) comprises six helices linked by short loops. FIG. 3A depicts a protein crystal structure ribbon representation of the hIL-10 monomer, wherein its six helices are labeled A-F, and FIG. 3B depicts a protein crystal structure ribbon representation of the hIL-10 homodimer, wherein the six helices of each monomer are labeled A-F.

Figure 3C:
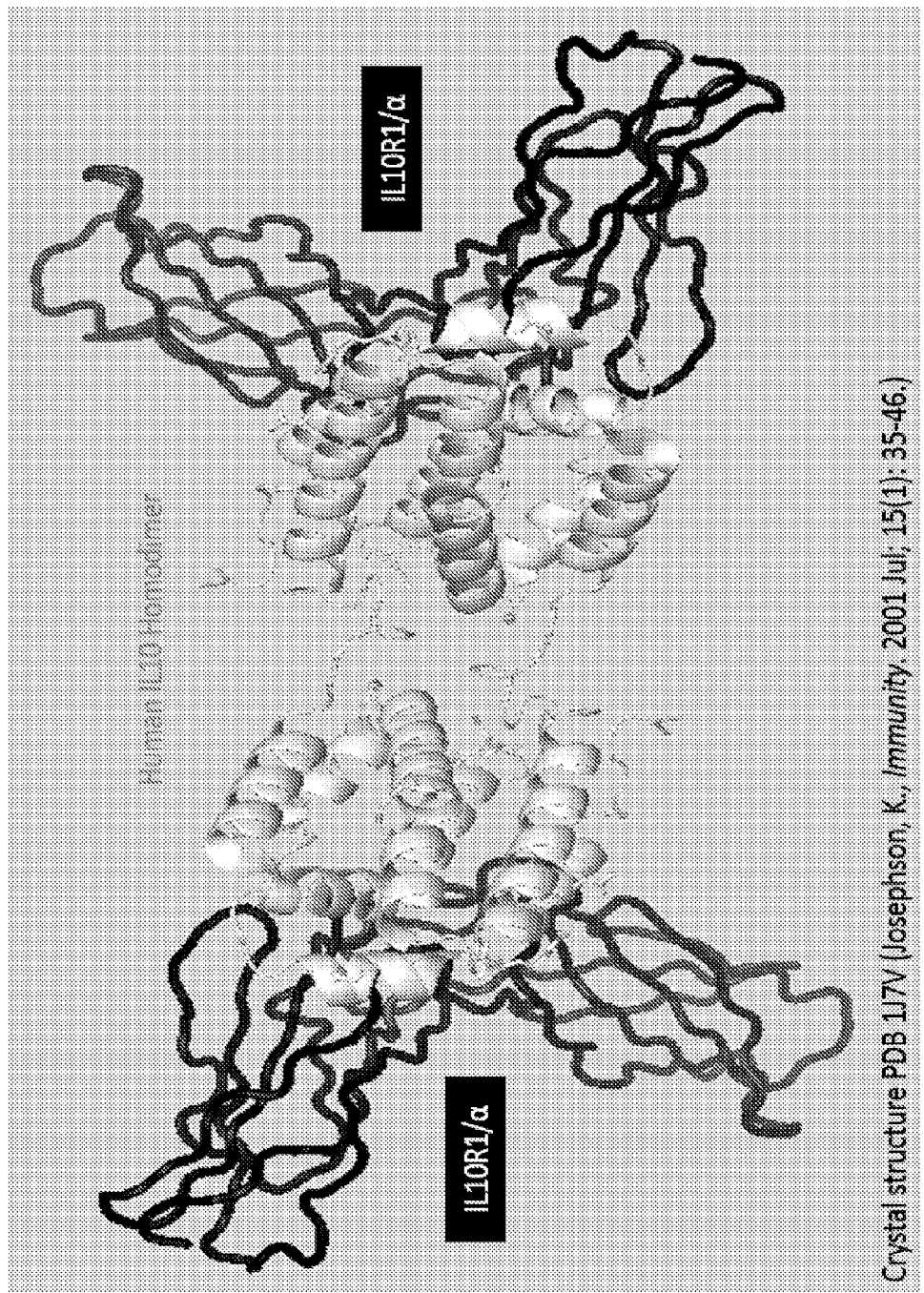
FIG. 3C is a protein crystal structure ribbon representation (top view) of the human IL-10 homodimer (gray) bound to two human IL10R1/α receptors (black).

The IL-10 receptor, a type II cytokine receptor, comprises alpha and beta subunits, which are also referred to as R1 and R2, respectively. While the mechanics of IL-10 receptor binding have not been thoroughly elucidated, it has been shown that IL-10 signaling requires contributions from both IL-10R1 and IL-10R2. This may occur through one IL-10 homodimer independently binding both IL-10R1 and IL-10R2 combined with some type of clustering event, or by one IL-10 homodimer forming a single complex with both IL-10R1 and IL-10R2. The crystal structure of the IL-10/IL-10R1 complex has been published (Josephson, K. et al., (2001) Immunity (1):35-46), and FIG. 3C depicts a protein crystal structure ribbon representation of the human IL10 homodimer (gray) bound to two human IL10R1/$\alpha$ receptors (black).

Also encompassed herein are other IL-10 molecules, including IL-10 fragments; polypeptides based on IL-10 monomers; molecules that comprise an IL-10 monomer complexed with a heterologous protein; and IL-10 fusion proteins that comprise IL-10 fused, at the nucleic acid level, to one or more therapeutic agents (e.g., an anti-inflammatory biologic). Such molecules may be modified using the approaches described herein or any other approach known to the skilled artisan.

As used herein, the term "pegylated IL-10" refers to an IL-10 molecule having one or more polyethylene glycol molecules covalently attached to at least one amino acid residue of the IL-10 protein, generally via a linker, such that the attachment is stable. The term "monopegylated IL-10"

indicates that one polyethylene glycol molecule is covalently attached to a single amino acid residue on one subunit of the IL-10 dimer, generally via a linker. In certain embodiments, the pegylated IL-10 used in the present disclosure is a mono-pegylated IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing a pegylation reaction to proceed to completion will generally result in non-specific and multi-pegylated IL-10, thus reducing its bioactivity. Some embodiments of the present disclosure comprise the administration of a mixture of mono- and di-pegylated IL-10 produced by the methods described herein.

In particular embodiments, the average molecular weight of the PEG moiety is between about 5 kDa and about 50 kDa. For example, the PEG moiety may have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Although the present disclosure does not require use of a specific method or site of PEG attachment to IL-10, it is frequently advantageous that pegylation does not alter, or only minimally alters, the activity of the IL-10 molecule. In certain embodiments, the increase in half-life achieved by pegylation is greater than any decrease in biological activity. In particular embodiments, lot release and PEG-IL-10 biological activity are measured using an MC/9 Cell Proliferation Assay, an example of which is set forth in the Experimental section. In some embodiments, the biological activity of PEG-IL-10 is measured by assessing the levels of inflammatory cytokines (e.g., TNF-α or IFN-γ) in the serum of subjects challenged with a bacterial antigen (lipopolysaccharide (LPS)) and treated with PEG-IL-10, as described in U.S. Pat. No. 7,052,686. Additional aspects of pegylation are described further hereafter.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions may be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution. If should be noted that one or more unnatural amino acids may be introduced into IL-10 as a way of fostering site-specific conjugation.

The present disclosure also contemplates active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides may be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides may be isolated from a natural source (e.g., an environment other than its naturally-occurring environment) and may also be recombinantly made (e.g., in a genetically modified host cell such as bacteria, yeast, *Pichia*, insect cells, and the like), where the genetically modified host cell is modified with a nucleic acid comprising a nucleotide sequence encoding the polypeptide. The IL-10 polypeptides may also be synthetically produced (e.g., by cell-free chemical synthesis).

Nucleic acid molecules encoding the IL-10 molecules are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

Methods of Production of IL-10

A polypeptide of the present disclosure can be produced by any suitable method, including non-recombinant (e.g., chemical synthesis) and recombinant methods.

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as 9-fluorenyl-methoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

B. Recombinant Production

Methods describing the preparation of human (and mouse) IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248:1230. IL-10 can be obtained in a number of ways using standard techniques known in the art, such as those described herein. Recombinant human IL-10 is also commercially available, e.g., from PeproTech, Inc., Rocky Hill, N.J.

Site-specific mutagenesis (also referred to as site-directed mutagenesis and oligonucleotide-directed mutagenesis) can be used to generate specific mutations in DNA to produce rationally-designed proteins of the present disclosure (e.g., particular IL-10 muteins and other modified versions of IL-10, including domains thereof) having improved or desirable properties. Techniques for site-specific mutagenesis are well known in the art. Early site-specific mutagenesis methods (e.g., Kunkel's method; cassette mutagenesis; PCR site-directed mutagenesis; and whole plasmid mutagenesis, including SPRINP) have been replaced by more precise and efficient methods, such as various in vivo methods that include Delitto perfetto (see Storici F. and Resnick M A, (2006) Methods in Enzymology 409:329-45); transplacement "pop-in pop-out"; direct gene deletion and site-specific mutagenesis with PCR and one recyclable marker; direct gene deletion and site-specific mutagenesis with PCR and one recyclable marker using long homologous regions; and in vivo site-directed mutagenesis with synthetic oligonucleotides (and see, e.g., In Vitro Mutagenesis Protocols (Methods in Molecular Biology), 2nd Ed. ISBN 978-0896039100). In addition, tools for effecting site-specific mutagenesis are commercially available (e.g., Stratagene Corp., La Jolla, Calif.).

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide may be generated using recombinant techniques to manipulate different IL-10—related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Modifications of IL-10

A. Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other sources of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —CH$_2$NH—, —CH$_2$S—, —CH$_2$CH$_2$—, —CH=CH—(cis and trans), —COCH$_2$—, —CH(OH)CH$_2$— or —CH$_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

B. Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. In some embodiments, IL-10 comprises only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, w-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

C. Additional Modifications of IL-10

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art (see, e.g., U.S. Pat. No. 8,067,532).

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other methods of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —(CH2)$_n$-CO— or —(CH2)$_n$-C$_6$H$_4$—CO—) with functional groups which allow for the introduction of a bridge. Some examples are disulfides, disulfide mimetics such as the —(CH2)$_n$- carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:4); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:5); Transportan GWTLN-SAGYLLGKINLKALAALAKKIL (SEQ ID NO:6); KALAWEAKLAKALAKALAKHLAKALAKALKCEA (SEQ ID NO:7); and RQIKIWFQNRRMKWKK (SEQ ID NO:8). Exemplary PTDs include, but are not limited to, YGRKKRRQRRR (SEQ ID NO:4), RKKRRQRRR (SEQ ID NO:9); an arginine homopolymer of from 3 arginine residues to 50 arginine residues; exemplary PTD domain amino acid sequences include, but are not limited to, any of the following: YGRKKRRQRRR (SEQ ID NO:4); RKKRRQRR (SEQ ID NO:10); YARAAARQARA (SEQ ID NO:11); THRLPRRRRRR (SEQ ID NO:12); and GGR-RARRRRRR (SEQ ID NO:13).

The carboxyl group $COR_3$ of the amino acid at the C-terminal end of an IL-10 polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of an IL-10 polypeptide can be present in a free form ($R_1$=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

D. Pegylation and Other Modifications to Enhance and/or Mimic IL-10 Function

It is frequently beneficial, and sometimes imperative, to improve one of more physical properties of the treatment modalities disclosed herein (e.g., IL-10 molecules) and/or the manner in which they are administered. Improvements of physical properties include, for example, modulating immunogenicity; methods of increasing solubility, bioavailability, plasma half-life; and modulating biological activity. Certain modifications may also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity. Modifications of the IL-10 molecules contemplated by the present disclosure include, but are not limited to, pegylation, glycosylation (N— and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

In particular embodiments, the IL-10 molecules are modified by conjugating or linking a polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability; protection against susceptibility to enzymatic degradation; increased solubility; longer plasma half-life and decreased clearance; reduced immunogenicity and antigenicity; and reduced toxicity.

In addition to the beneficial effects of pegylation on pharmacokinetic parameters, pegylation itself may enhance activity. For example, pegylated IL-10 has been shown to be more efficacious against certain cancers than unpegylated IL-10 (see, e.g., EP 206636A2).

The therapeutic value of pegylation molecules is well validated. Previous and/or current pharmaceutical products include: OMONTYS (Affymax/Takeda); PEGLOTICASE (Savient); CIMZIA (Nektar/UCB Pharma); MACUGEN (Prizer); NEULASTA (Amgen); SOMAVERT (Prizer); PEGASYS (Roche); DOXIL (Ortho Biotech) and PEGIN-TRON (Schering-Plough).

PEGs suitable for conjugation to a polypeptide sequence are generally soluble in water at room temperature, and have the general formula R(O—$CH_2$—$CH_2$)$_n$O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight (molecular mass) of the PEG used in the present disclosure is not restricted to any particular range. Certain embodiments have molecular weights between 5 kDa and 20 kDa, while other embodiments have molecular weights between 4 kDa and 10 kDa. PEGs having additional molecular weights are described elsewhere herein.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography may be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein. PEG may be bound to a polypeptide of the present disclosure via a terminal reactive group (a "spacer") which mediates a bond between the free amino or carboxyl groups of one or more of the polypeptide sequences and polyethylene glycol. The PEG having the spacer which may be bound to the free amino group includes N-hydroxysuccinylimide polyethylene glycol, which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from, e.g., 1:1; 1.5:1; 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various methods known in the art may be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. Pegylated IL-10 is described in, e.g., U.S. Pat. No. 7,052,686. Particular reaction conditions contemplated for use herein are set forth in the Experimental section.

As indicated above, pegylation most frequently occurs at the N-terminus, the side chain of lysine residues, and the imidazole group on the side chain of histidine residues. The usefulness of such pegylation has been enhanced by refinement by, for example, optimization of reaction conditions and improvement of purification processes. More recent residue-specific chemistries have enabled pegylation of arginine, aspartic acid, cysteine, glutamic acid, serine, threonine, and tyrosine, as well as the carboxy-terminus. Some of these amino acid residues can be specifically pegylated, while others are more promiscuous or only result in site-specific pegylation under certain conditions.

Current approaches allowing pegylation of additional amino acid residues include bridging pegylation (disulfide bridges), enzymatic pegylation (glutamines and C-terminus) and glycopegylation (sites of O— and N-glycosylation or the glycans of a glycoprotein), and heterobifunctional pegylation. Further approaches are drawn to pegylation of proteins containing unnatural amino acids, intein fusion proteins for C-terminal pegylation, transglutaminase-mediated pegylation, sortase A-mediated pegylation, and releasable and non-covalent pegylation. In addition, combination of specific pegylation approaches with genetic engineering techniques has enabled the polyethylene glycan polymer to essentially couple at any position on the protein surface due to, for example, substitution of specific amino acid residues in a polypeptide with a natural or unnatural amino acid bearing an orthogonal reactive group. See generally, e.g., Pasut, G. and Veronese, F. M., (2012) J. Controlled Release 161:461-72; Roberts, M. J. et al., (2012) Advanced Drug Delivery Rev. 64:116-27; Jevsevar, S. et al., (2010) Biotechnol. J. 5:113-28; and Yoshioka, Y. (2011) Chem. Central J. 5:25.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Any of the foregoing components and molecules used to modify the polypeptide sequences of the present disclosure (e.g., polyethylene glycol) may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Exemplary flexible linkers include glycine polymers $(G)_n$, glycine-serine polymers (for example, $(GS)_n$, $GSGGS_n$, (SEQ ID NO:14) and $GGGS_n$ (SEQ ID NO:15), where n is an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:16), GGSGG (SEQ ID NO:17), GSGSG (SEQ ID NO:18), GSGGG (SEQ ID NO:19), GGGSG (SEQ ID NO:20), and GSSSG (SEQ ID NO:21).

Release Assays

Because biologic agents are sensitive to changes in the starting materials and manufacturing processes used in their production, they may be difficult to consistently produce and characterize. As such, biologics are subject to additional regulatory requirements and oversight than small molecules, which are generally synthesized by precise chemical methods. Lot release assessments are used to ensure that biologics within each batch, or "lot", possess the requisite potency (which is tied to, e.g., biostability), consistently contain the same API and are safe for human use.

As set forth herein, a biologic is assessed based on parameters that are specific for it, including: source and level of control of the raw materials; complexity, robustness and level of control of the manufacturing process; chemical complexity of the drug substance and the drug product; and reliability and complexity of the methods used to evaluate identity, purity, and potency of the drug substance and the drug product.

Peptide Mapping

The production of biologics requires very rigorous quality control due to the potential for undesirable protein modifications and contamination. An element of this rigorous quality control entails confirmation of the integrity of the amino acid sequence for each production batch (lot) of a protein biologic. Peptide mapping (also referred to as "peptide mass fingerprinting") is a powerful method for the structural determination and confirmation of protein biologics' sequence identity and is an indispensable analytical method for the quality control of recombinantly-derived proteins.

A peptide map is essentially a "fingerprint" of a protein resulting from several chemical processes that provide a comprehensive understanding of the protein being analyzed. At its most basic level, peptide mapping involves enzymatic digestion or chemical cleavage of a protein, separation of the resulting fragments, and analysis of the fragments. The method can be used to confirm that a protein is, in fact, the protein of interest without the need to perform time-consuming peptide sequencing.

Examples of enzymatic digestion and chemical cleavage agents are set forth in Table 1.

TABLE 1

| | Agent | Specificity |
|---|---|---|
| Enzymatic | Trypsin | C-terminal side of Arg and Lys |
| | Chymotrypsin | C-terminal side of hydrophobic residues (e.g., Leu, Met, Ala, aromatics) |
| | Pepsin | Non-specific agent |
| | Lysyl endopeptidase (Lys-C Endopeptidase; Endo Lys-C) | C-terminal side of Lys |
| | Glutamyl endopeptidase (from *S. aureus* strain V8; Endo Glu-C) | C-terminal side of Glu and Asp |
| | Peptidyl-Asp metallo endopeptidase (Endopeptidase Asp-N; Endo Asp-N) | N-terminal side of Asp |
| | Clostripain | C-terminal side of Arg |
| Chemical | Cyanogen bromide | C-terminal side of Met |

TABLE 1-continued

| Agent | Specificity |
|---|---|
| 2-nitro-5-thio-cyanobenzolic acid | N-terminal side of Cys |
| O-iodsobenzoic acid | C-terminal side of Trp and Tyr |
| Dilute Acid | Asp and Pro |
| BNPS-skatole | Trp |

Techniques used for the separation of peptides produced by digestion and cleavage include: RP-HPLC; IEC; HIC; PAGE; SDS-PAGE; CE; PCHV electrophoresis; and HVPE.

The absolute masses of the fragments are determined by a mass spectrometer (e.g., ESI-MS, ESI-MS/MS, ESI-TOF MS, MALDI MS and MALDI-TOF MS) and then compared to peptide masses previously determined for known proteins (e.g., protein-specific peptide mass data stored in a computer database). In the present context, the measured peptide masses are generally compared to those previously determined for IL-10 using methodologies analogous to those described above. As with other mass spectrometry-based analytical proteomics techniques, the quality of protein identification depends on the quality of the MS data itself, the accuracy of the databases, and the power of the search algorithms and software used.

To enable optimal analysis, the desired size range of peptides produced by enzymatic digestion was historically about 600-5,000 Da. However, the size range has increased to about 600-20,000 Da due to recent advancements in software and mass spectrometry techniques (e.g., electron transfer dissociation (ETD) and electron capture dissociation (ECD)), along with the potential for combination with collision-activated dissociation (CAD). Nonetheless, some peptides still fall above or below the desired peptide size range, resulting in decreased protein coverage and incomplete data collection.

Protein digestion with trypsin ("tryptic mapping"; described further below) is the primary method for protein analysis. In order to increase protein coverage, alternative proteinases have been introduced. The use of alternative proteinases, individually or in combination with other proteinases, creates a unique peptide map that may include peptide sequences not seen in trypsin digestions. Moreover, overlaying peptides obtained from digestion with alternative proteinases increases protein coverage and overall confidence in protein identification. Through the use of alternative enzymes, peptides that are too large for optimal use with particular analytical instrumentation may be cleaved into smaller, more manageable fragments.

Alternative proteinases may also be helpful in overcoming incomplete digestion caused by PTMs, which prevent the proteinases from accessing a necessary site, and in identifying translocation partners.

Tryptic Mapping. As indicated herein, protein digestion with trypsin ("tryptic mapping") is the primary method for protein structural determination (including, e.g., newly discovered proteins). Enzymatic digestion with trypsin is advantageous because it cleaves at the C-terminal side of Lys and Arg residues, which is generally quantitative under proper conditions, because it tolerates concentrations of urea as high as 4M, and because it can be used to locate glycosylation sites and disulfide linkages. Tryptic mapping provides information on lot-to-lot product consistency, expression errors, mutation and deamination sites, and it is increasingly used in biotechnology for quality control of recombinant proteins.

Despite its widespread use, tryptic mapping is not without limitations and shortcomings. It requires a high level of column resolution and system precision for accurate reproduction of the maps. Furthermore, because of large number of peaks in a tryptic map, it is difficult to identify fragments contributed by a contaminant protein at a level of 1-5%. Moreover, tryptic digest of certain pegylated proteins does not yield reproducible and/or meaningful data.

Endoproteinase Glu-C Mapping. As set forth in Table 1, endoproteinase Glu-C (Endo Glu-C) is an alternative enzyme for protein digestion. Endo Glu-C is a recombinantly produced serine protease (Staphylococcus aureus Protease V8 gene cloned and expressed in Bacillus subtilis) that cleaves proteins with high specificity at the C-terminus of glutamic acid and aspartic acid residues, and thus creates unique peptide fragments available for mass spectrometry analysis. Although Endo Glu-C has been used in protein characterization for several decades, its importance has recently increased due to advancements in mass spectrometry techniques. Endo Glu-C reagents are commercially available from a number of sources, including New England BioLabs (Ipswich, Mass.) and Worthington Biochemical Corp. (Lakewood, N.J.).

The Endo Glu-C amino acid sequence is set forth in FIG. 2. It contains a 6-His-Tag on the C-terminus of the protein. Endo Glu-C appears as a single band on SDS-PAGE, and a small amount of the enzyme may contain two additional Ala residues at its N-terminus.

Endo Glu-C cleaves at aspartic acid residues at a rate 100-300 times slower than at glutamic acid residues. Furthermore, the specificity of Endo Glu-C is influenced by the buffer composition; in phosphate buffers, both glutamic and aspartic residues are cleaved, while in ammonium bicarbonate and ammonium acetate buffers (pH 4.0), only the glutamic residues are cleaved.

Digestion of IL-10 and Pegylated IL-10

Fragmentation of IL-10, PEG-IL-10, and the other IL-10—related molecules described herein may be effected by enzymatic and chemical digestion. The agents set forth above in Table 1 may be evaluated as fragmentation candidates. Although other factors may be relevant, a digestion of IL-10 that results in a peptide map containing fewer, more discrete peptide members compared to the peptide members resulting from a different digestion is easier to interpret across different lots and conditions.

Particular embodiments of the present disclosure contemplate digestion with a proteolytic agent, such as a peptidase. In some embodiments, the peptidase is trypsin, while in other embodiments the peptidase is Endo Glu-C. Each monomer of the human IL-10 dimeric structure has 17 Endo Glu-C digestion sites (i.e., glutamic acid and aspartic acid residues) and 21 trypsin digestion sites. Thus, digestion with Endo Glu-C results in fewer peptide fragments and a simpler digest to interpret. Fewer peptide fragments also translate into potentially fewer problems during critical release testing. In addition, the data resulting from digestion with Endo Glu-C is more robust (e.g., more distinct peaks produced by mass spectrometry) than that resulting from digestion with trypsin Peptide mapping of a pegylated protein is often associated with considerations that are not present with peptide mapping of the corresponding unpegylated protein. PEG-IL-10 digestion with Endo-Glu-C provides superior results to that with trypsin. Essentially, the PEG-IL-10 tryptic map will not provide a consistent "map" of the mixed di- and mono-pegylated IL-10 to provide reproducibility for setting specifications for bulk drug substance (BDS) and final drug product (DP) release criteria. Of particular import with regards to PEG-IL-10, digestion with Endo Glu-C yields consistent and reproducible data generated by a lot release assay. Such consistency and reproducibility is observed regardless of whether an individual performs the release assay using different equipment; a different individual performs the release assay using the same equipment as the first individual; or a different individual performs the release assay using different machinery than the first individual.

Figure 4:
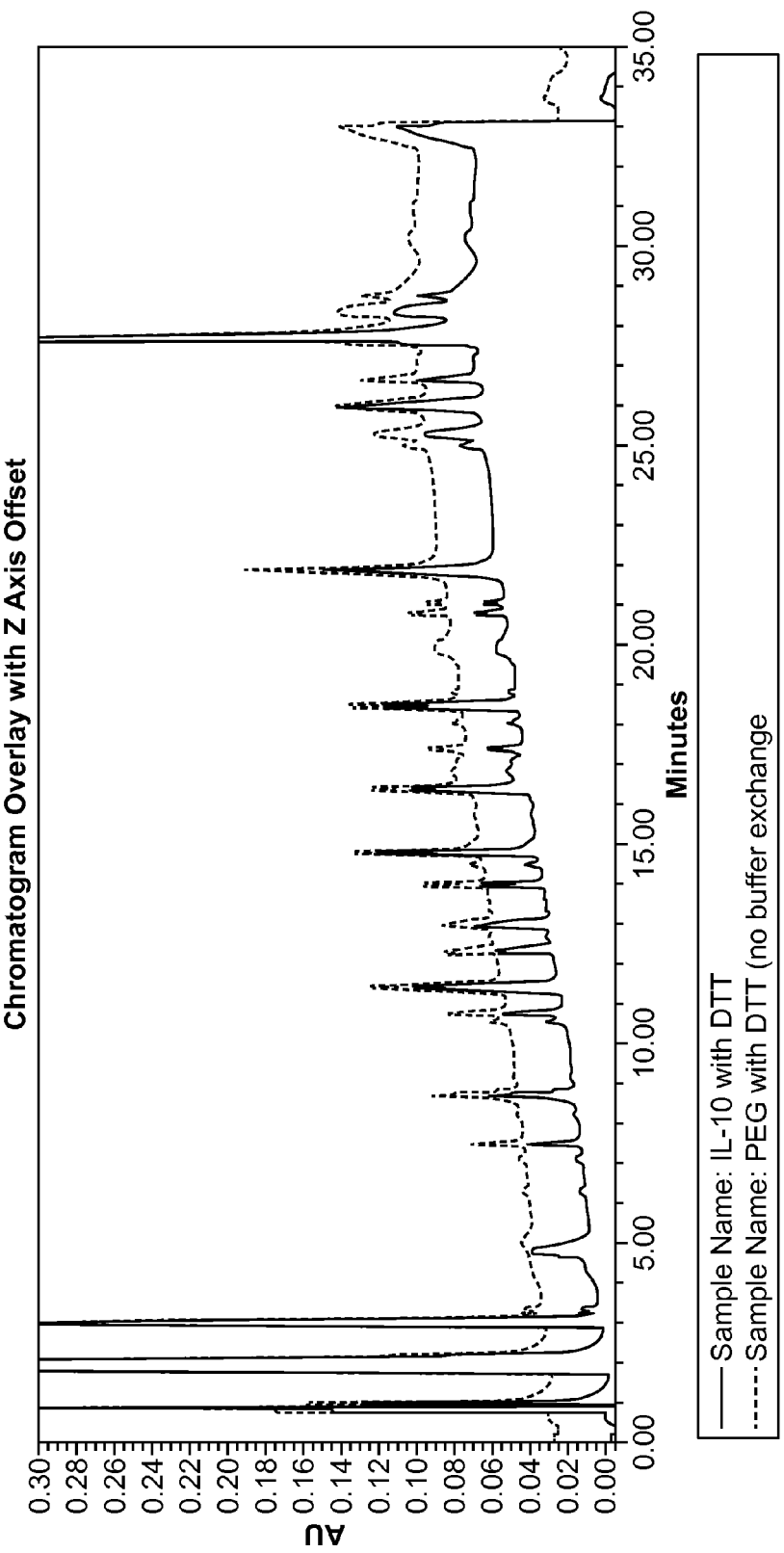
FIG. 4 is a chromatogram depicting an Endo Glu-C digest and UV-detected peptide map of rhIL-10 (dark trace) and PEG-rhIL-10 (light trace).

Digestion of IL-10 and PEG-IL-10 with the Endo Glu-C peptidase provides more robust and reproducible data than digestion with trypsin. Using the methodology described in the Experimental section, an Endo Glu-C digest and UV-detected peptide map of IL-10 and PEG-IL-10 resulted in discrete and readily interpretable peaks (see FIG. 4). The chromatogram set forth in FIG. 4 also indicates that the peptide map exhibits substantially similar traces for rhIL-10 (dark trace) and PEG-rhIL-10 (light trace). Of note, the use of ESI-MS/MS following Endo Glu-C digestion of PEG-IL yielded a peptide map having discrete peaks, but of insufficient resolution to readily characterize the PEG moiety. The skilled artisan will be able to evaluate other detection methods that can be employed with Endo Glu-C.

As noted above, digestion of IL-10 with trypsin produces more peptide fragments than digestion with Endo Glu-C. This increased number of peptide fragments necessitates additional, time-intensive interpretation. In addition, mass spectrometry (e.g., ESI-MS/MS) of the trypsin-produced peptide fragments results in peaks that are less discrete.

Thus, the Endo Glu-C peptidase provides robust and consistent results as to the identity (e.g., amino acid sequence) and stability of compositions comprising pegylated interleukin-10 and other pegylated interleukin-10—related molecules. As a result, digestion with Endo Glu-C is ideal as a lot release assay for PEG-rhIL-10.

Therapeutic and Prophylactic Uses

The present disclosure contemplates the use of the IL-10 molecules (e.g., PEG-IL-10) described herein in the treatment or prevention of a broad range of diseases, disorders and/or conditions, and/or the symptoms thereof. While particular uses are described in detail hereafter, it is to be understood that the present disclosure is not so limited. Furthermore, although general categories of particular diseases, disorders and conditions are set forth hereafter, some of the diseases, disorders and conditions may be a member of more than one category (e.g., cancer- and fibrotic-related disorders), and others may not be a member of any of the disclosed categories.

The present disclosure contemplates embodiments wherein an IL-10 (e.g., PEG-IL-10) agent is used as a diagnostic or as a component thereof. In further embodiments, the present disclosure provides methods for treating a proliferative condition, cancer, tumor, or precancerous condition with an IL-10 molecule and at least one additional therapeutic or diagnostic agent, examples of which are set forth elsewhere herein.

Fibrotic Disorders and Cancer. In accordance with the present disclosure, the IL-10 molecules (e.g., PEG-IL-10) described herein can be used to treat or prevent proliferative diseases, disorders or conditions, including cancers and cancer-related diseases, disorders or conditions. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

Cardiovascular Diseases and Cholesterol-related Disorders. The present disclosure also contemplates the use of the IL-10 agents (PEG-IL-10) described herein to treat and/or prevent certain cardiovascular- and/or associated metabolic-related diseases, disorders and conditions, as well as disorders associated therewith.

As used herein, the terms "cardiovascular disease", "heart disease" and the like refer to any disease that affects the cardiovascular system, primarily cardiac disease, vascular diseases of the brain and kidney, and peripheral arterial diseases. Cardiovascular disease is a constellation of diseases that includes coronary heart disease (i.e., ischemic heart disease or coronary artery disease), atherosclerosis, cardiomyopathy, hypertension, hypertensive heart disease, cor pulmonale, cardiac dysrhythmias, endocarditis, cerebrovascular disease, and peripheral arterial disease. Cardiovascular disease is the leading cause of deaths worldwide, and while it usually affects older adults, the antecedents of cardiovascular disease, notably atherosclerosis, begin in early life.

Particular embodiments of the present disclosure are directed to the use of IL-10 polypeptides to treat and/or prevent atherosclerosis, a chronic condition in which an artery wall thickens to form plaques as a result of the accumulation of fatty materials such as cholesterol and triglycerides. Atherosclerosis frequently involves a chronic inflammatory response in the walls of arteries, caused largely by the accumulation of macrophages and promoted by low-density lipoproteins (LDL) without adequate removal of fats and cholesterol from the macrophages by functional high-density lipoproteins. Chronically expanding atherosclerotic lesions can cause complete closure of the lumen, which may only manifest when the lumen stenosis is so severe that blood supply to downstream tissue(s) is insufficient, resulting in ischemia.

The IL-10 polypeptides may be particularly advantageous in the treatment and/or prevention of cholesterol-related disorders, which may be associated with, for example, cardiovascular disease (e.g. atherosclerosis), cerebrovascular disease (e.g., stroke), and peripheral vascular disease. By way of example, but not limitation, the IL-10 polypeptides may be used for lowering a subject's blood cholesterol level. In determining whether a subject has hypercholesterolemia, there is no firm demarcation between normal and abnormal cholesterol levels, and interpretation of values needs to be made in relation to other health conditions and risk factors. Nonetheless, the following guidelines are generally used in the United States: total cholesterol <200 mg/dL is desirable, 200-239 mg/dL is borderline high, and ≥240 mg/dL is high. Higher levels of total cholesterol increase the risk of cardiovascular disease, and levels of LDL or non-HDL cholesterol are both predictive of future coronary heart disease. When assessing hypercholesterolemia, it is frequently useful to measure all lipoprotein subfractions (VLDL, IDL, LDL and HDL). A particular therapeutic goal is to decrease LDL while maintaining or increasing HDL.

Thrombosis and Thrombotic Conditions. Thrombosis, the formation of a thrombus (blood clot) inside a blood vessel resulting in obstruction of the flow of blood through the circulatory system, may be caused by abnormalities in one or more of the following (Virchow's triad): hypercoagulability, endothelial cell injury, or disturbed blood flow (stasis, turbulence).

Thrombosis is generally categorized as venous or arterial, each of which can be presented by several subtypes. Venous thrombosis includes deep vein thrombosis (DVT), portal vein thrombosis, renal vein thrombosis, jugular vein thrombosis, Budd-Chiari syndrome, Paget-Schroetter disease, and cerebral venous sinus thrombosis. Arterial thrombosis includes stroke and myocardial infarction.

Other diseases, disorders and conditions are contemplated by the present disclosure, including atrial thrombosis and Polycythemia vera (also known as erythema, primary polycythemia and polycythemia rubra vera), a myeloproliferative blood disorder in which the bone marrow makes too many RBCs, WBCs and/or platelets.

Furthermore, blood vessels injured by, for example, cholesterol or smoking develop plaques, which can rupture and cause the plaques to form a clot. This response occurs even though no bleeding is occurring.

Immune and Inflammatory Conditions. As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

A non-limiting list of immune- and inflammatory-related diseases, disorders and conditions which may, for example, be caused by inflammatory cytokines, include arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Viral Diseases. There has been increased interest in the role of IL-10 in viral diseases. IL-10 has been postulated to produce both stimulatory and inhibitory effects depending on, for example, its receptor binding activity.

The effect of inhibiting IL-10 function in order to increase antiviral immunity and vaccine efficacy has been considered (see Wilson, E., (2011) Curr. Top. Microbiol. Immunol. 350:39-65). Moreover, the role of IL-10 in human immunodeficiency virus (HIV) function has been studied. In addition to the inhibition of human immunodeficiency virus type 1 (HIV-1) replication, IL-10 may also promote viral persistence by inactivation of effector immune mechanisms (Naicker, D., et al., (2009) J. Infect. Dis. 200 (3):448-452). Another study has identified an IL-10—producing subset of B-cells able to regulate T-cell immunity in chronic hepatitis B virus (HBV) infection. A close temporal correlation was observed between IL-10 levels and fluctuations in viral load, and in vitro blockade of IL-10 was found to rescue polyfunctional, virus-specific CD8+ T-cell responses (Das, A., et al., J. Immunol., Sep. 12, 2012 1103139 (on-line)).

Although the aforementioned studies indicate that IL-10 inhibition may be beneficial, particular viral infections that comprise a CD8+ T-cell component may be candidates for treatment and/or prevention through the administration of an IL-10 agent (e.g., PEG-IL-10). This is supported by the positive role that IL-10 plays in certain cancers by modulation of regulatory T cells and/or CD8+ T cells. The use of IL-10 therapy in viral contexts has also been discussed elsewhere (see, e.g., J. Virol. July 2011 vol. 85 no. 14 6822-683; and Loebbermann J, et al. (2012) PLoS ONE 7(2): e32371. doi:10.1371/journal.pone.0032371).

The present disclosure contemplates the use of the IL-10 molecules (e.g., PEG-IL-10) in the treatment and/or prevention of any viral disease, disorder or condition for which treatment with IL-10 may be beneficial. Examples of viral diseases, disorders and conditions that are contemplated include hepatitis B, hepatitis C, HIV, herpes virus and cytomegalovirus (CMV).

Routes of Administration and Pharmaceutical Compositions

The IL-10 molecules (e.g., PEG-IL-10) of the present disclosure may be in the form of compositions suitable for administration to a subject. In general, such compositions are "pharmaceutical compositions" comprising an IL-10 agent as described herein and one or more pharmaceutically or physiologically acceptable diluents, carriers or excipients. In certain embodiments, the IL-10 agent is present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration. The present disclosure contemplates the administration of the IL-10 molecules (e.g., PEG-IL-10) described herein, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Particular embodiments of the present disclosure contemplate parenteral administration, and in further particular embodiments the parenteral administration is subcutaneous.

The skilled artisan is familiar with methodologies for preparing pharmaceutical compositions and the various components thereof. The pharmaceutical compositions typically comprise a therapeutically effective amount of an IL-10 agent (e.g., PEG-IL-10) and one or more pharmaceutically and physiologically acceptable diluents, carriers or excipients including, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants.

For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver IL-10, including implants (e.g., implantable pumps) and catheter systems, slow injection pumps and devices, all of which are well known to the skilled artisan.

Depot injections, which are generally administered subcutaneously or intramuscularly, may be utilized to release the IL-10 molecules disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be used, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

Pharmaceutical compositions comprising the IL-10 molecules contemplated herein may be in other dosage forms, including dosage forms suitable for alternative routes of administration, currently known or developed in the future. For example, the IL-10 molecules may be in the form of tablets or capsules suitable for oral administration, suppositories for rectal administration, and sprays for nasal or inhalation use.

The concentration of an IL-10 agent in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Combination Therapy

The present disclosure contemplates the use of IL-10 molecules (e.g., PEG-IL-10) in combination with one or more active therapeutic agents (e.g., cytokines) or other prophylactic or therapeutic modalities (e.g., radiation) in order to treat or prevent the diseases, disorders and conditions as contemplated by the present disclosure. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IL-10 polypeptides (e.g., PEG-IL-10) are administered or applied sequentially, e.g., where one agent is administered prior to one or more other agents. In other embodiments, the IL-10 polypeptides are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The IL-10 polypeptides (e.g., PEG-IL-10) of the present disclosure may be used in combination with at least one other (active) agent, including pharmaceutically acceptable salts, acids or derivatives thereof, in any manner appropriate under the circumstances. In one embodiment, treatment with the at least one active agent and at least one IL-10 polypeptide of the present disclosure is maintained over a period of time. In another embodiment, treatment with the at least one active agent is reduced or discontinued (e.g., when the subject is stable), while treatment with the IL-10 polypeptide of the present disclosure is maintained at a constant dosing regimen. In a further embodiment, treatment with the at least one active agent is reduced or discontinued (e.g., when the subject is stable), while treatment with the IL-10 polypeptide of the present disclosure is reduced (e.g., lower dose, less frequent dosing or shorter treatment regimen). In yet another embodiment, treatment with the at least one active agent is reduced or discontinued (e.g., when the subject is stable), and treatment with the IL-10 polypeptide of the present disclosure is increased (e.g., higher dose, more frequent dosing or longer treatment regimen). In yet another embodiment, treatment with the at least one active agent is maintained and treatment with the IL-10 polypeptide of the present disclosure is reduced or discontinued (e.g., lower dose, less frequent dosing or shorter treatment regimen). In yet another embodiment, treatment with the at least one active agent and treatment with the IL-10 polypeptide of the present disclosure are reduced or discontinued (e.g., lower dose, less frequent dosing or shorter treatment regimen).

The present disclosure contemplates the use of IL-10 molecules (e.g., PEG-IL-10) in combination with one or more prophylactic or therapeutic modalities (now known or developed in the future), including modalities useful in the treatment, prevention, and/or diagnosis of fibrotic disorders and cancer (including proliferative conditions); immune and inflammatory conditions; viral diseases; and thrombotic disorders.

In addition, some embodiments are directed at combination therapy for the treatment, prevention, and/or diagnosis of cardiovascular diseases. By way of example, and not limitation, an IL-10 agent (e.g., PEG-IL-10) may be used in combination with modalities for the treatment of hypercholesterolemia (as well as atherosclerosis) including statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the IL-10 polypeptides described herein include inhibitors of Proprotein Convertase Subtilisin Kexin 9 (PCSK9) for the treatment of hypercholesterolemia and related pathologies. Such modalities include monoclonal antibodies (mAb), antisense RNAi, small molecules, and the use of recombinant adnectins.

Dosing

The IL-10 polypeptides (e.g., PEG-IL-10) of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IL-10 molecules (e.g., PEG-IL-10) of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

The amount of an IL-10 (e.g., PEG-IL-10) molecule necessary to treat a disease, disorder or condition described herein is based on the IL-10 activity of the conjugated protein, which can be determined by IL-10 activity assays known in the art. By way of example, in the tumor context suitable IL-10 activity includes, for example, CD8+ T-cell infiltration into tumor sites, expression of inflammatory cytokines, such as IFN-γ, IL-4, IL-6, IL-10, and RANK-L, from these infiltrating cells, and increased levels of TNF-α or IFN-γ in biological samples.

The therapeutically effective amount of an IL-10 molecule can range from about 0.01 to about 100 μg protein/kg of body weight/day, from about 0.1 to 20 μg protein/kg of body weight/day, from about 0.5 to 10 μg protein/kg of body weight/day, or about 1 to 4 μg protein/kg of body weight/day. In some embodiments, an IL-10 molecule is administered by continuous infusion to delivery about 50 to 800 μg protein/kg of body weight/day (e.g., about 1 to 16 μg protein/kg of body weight/day of an IL-10 molecule). The infusion rate may be varied based on evaluation of, for example, adverse effects and blood cell counts. In particular embodiments, the PEG-IL-10 molecule is administered subcutaneously.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the disclosed IL-10 polypeptide is contained in a "unit dosage form". The phrase "unit dosage form" refers to physically discrete units, each unit containing a predetermined amount of an IL-10 polypeptide of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising IL-10 (e.g., PEG-IL-10), and pharmaceutical compositions thereof. The kits are generally in the form of a physical structure housing various components, as described below, and may be utilized, for example, in practicing the methods described above (e.g., administration of an IL-10 molecule to a subject in need of restoring cholesterol homeostasis).

A kit can include one or more of the IL-10 polypeptides disclosed herein (provided in, e.g., a sterile container), which may be in the form of a pharmaceutical composition suitable for administration to a subject. The IL-10 polypeptides can be provided in a form that is ready for use or in a form requiring, for example, reconstitution or dilution prior to administration. When the IL-10 polypeptides are in a form that needs to be reconstituted by a user, the kit may also include buffers, pharmaceutically acceptable excipients, and the like, packaged with or separately from the IL-10 polypeptides. When combination therapy is contemplated, the kit may contain the several agents separately or they may already be combined in the kit. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but guidance for obtaining the instructions from a remote source, e.g., via the internet, are provided.

EXAMPLES

The following examples are put forth so as to provide those of ordinary skill in the art with a complete disclosure and description of how to make and use the present invention, and are not intended to limit the scope of what is regarded to be the invention nor are they intended to represent that the experiments below were performed and are all of the experiments that may be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; μg=microgram; mg=milligram; g=gram; kg=kilogram; dl or dL=deciliter; μl or μL=microliter; ml or mL=milliliter; l or L=liter; nM=nanomolar; μM=micromolar; mM=millimolar; M=molar; kDa=kilodalton; i.m.=intramuscular(ly); i.p.=intraperitoneal(ly); s.c.=subcutaneous(ly); QD=daily;

BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-Hydroxysuccinimide; DMEM=Dulbeco's Modification of Eagle's Medium; GC=genome copy; ELISA=enzyme-linked immuno sorbent assay; EDTA=ethylenediaminetetraacetic acid; PMA=phorbol myristate acetate; rhIL-10=recombinant human IL-10; LPS=lipopolysaccarhide; ESI-MS=electrospray ionization mass spectrometry; ESI-MS/MS=ESI tandem mass spectrometry; TIC=total ion chromatography; ESI-TOF MS=ESI time of flight mass spectrometry; MALDI=matrix-assisted laser desorption/ionization mass spectrometry; MALDI-TOF MS=matrix-assisted laser desorption/ionisation-time of flight mass spectrometry; RP-HPLC=reverse-phase high performance liquid chromatography; IEC=ion-exchange chromatography; HIC=hydrophobic interaction chromatography; PAGE=polyacrylamide gel electrophoresis; SDS-PAGE=sodium dodecyl dulfate—PAGE; CE=capillary electrophoresis; PCHV=paper chromatography-high voltage electrophoresis; HVPE=high-voltage paper electrophoresis; PEG-rhIL-10DS=pegylated recombinant human interleukin 10 drug substance; Endo Glu-C=endoproteinase Glu-C; DTT=dithiothreitol; UV=ultraviolet.

Materials and Methods

The following general materials and methods may be used in the Examples below.

Standard methods in molecular biology are described (see, e.g., Sambrook and Russell (2001) Molecular Cloning, $3^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Louis et al. (2002) Basic Histology: Text and Atlas, McGraw-Hill, New York, N.Y.).

Depletion of immune cells (CD4$^+$ and CD8$^+$ T-cells) may be effected by antibody-mediated elimination. For example, 250 μg of CD4- or CD8-specific antibodies may be injected weekly, and cell depletions verified using FACS and IHC analysis.

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (Time-Logic Corp., Crystal Bay, Nev.)).

Immunocompetent Balb/C or B-cell—deficient Balb/C mice were obtained from The Jackson Lab., Bar Harbor, Me. and used in accordance with standard procedures (see, e.g., Martin et al (2001) Infect. Immun., 69(11):7067-73 and Compton et al. (2004) Comp. Med. 54(6):681-89). Other mice strains suitable for the experimental work contemplated by the present disclosure are known to the skilled artisan and are generally available from The Jackson Lab.

Unless otherwise indicated, PDV6 squamous cell carcinoma of the skin was used in the experiments described herein (see, e.g., Langowski et al. (2006) Nature 442:461-465). Other oncology-related models and cell lines, such as Ep2 mammary carcinoma, CT26 colon carcinoma, and 4T1 breast carcinoma models, may be used (see, e.g., Langowski et al. (2006) Nature 442:461-465) and are known to the skilled artisan. Non-oncology—related models and cell lines (e.g., models of inflammation) may also be used and are known to the skilled artisan.

Serum IL-10 concentration levels and exposure levels may be determined by standard methods used in the art. For example, a serum exposure level assay can be performed by collecting whole blood (~50 μl/mouse) from mouse tail snips into plain capillary tubes, separating serum and blood cells by centrifugation, and determining IL-10 exposure levels by standard ELISA kits and techniques.

Production of Pegylated IL-10

The present disclosure contemplates the synthesis of pegylated IL-10 by any methods known to the skilled artisan. The description hereafter of several alternative synthetic schemes for producing mono-pegylated IL-10 and a mix of mono-/di-pegylated IL-10 is meant to be illustrative only. While both mono-pegylated IL-10 and a mix of mono-/di-pegylated IL-10 have many comparable properties, a mix of selectively pegylated mono- and di-pegylated IL-10 improves the yield of the final pegylated product (see, e.g., U.S. Pat. No. 7,052,686 and US Pat. Publn. No. 2011/0250163).

In addition to leveraging her own skills in the production and use of PEGs (and other drug delivery technologies) suitable in the practice of the present disclosure, the skilled artisan is also familiar with many commercial suppliers of PEG-related technologies (and other drug delivery technologies). By way of example, NOF America Corp (Irvine, Calif.) supplies mono-functional Linear PEGs, bi-functional PEGs, multi-arm PESs, branched PEGs, heterofunctional PEGs, forked PEGs, and releasable PEGs; and Parchem (New Rochelle, N.Y.) is a global distributor of PEG products and other specialty raw materials.

Exemplary Pegylated IL-10 Synthetic Scheme No. 1. IL-10 may be dialyzed against 10 mM sodium phosphate at pH 7.0, 100 mM NaCl. The dialyzed IL-10 may then be diluted 3.2 times to a concentration of 4 mg/mL using the dialysis buffer. Prior to the addition of the linker, SC-PEG-12K (Delmar Scientific Labs; Maywood, Ill.), 1 volume of 100 mM Na-tetraborate at pH 9.1 can be added into 9 volumes of the diluted IL-10 to raise the pH of the IL-10 solution to 8.6. The SC-PEG-12K linker can be dissolved in the dialysis buffer and the appropriate volume of the linker solution (1.8 to 3.6 mole of linker/mole of IL-10) can be added into the diluted IL-10 solution to start the pegylation reaction. The reaction can be carried out at 5° C. in order to control the rate of the reaction. The reaction solution can be mildly agitated during the pegylation reaction. When the mono-pegylated IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction solution is then filtered using a 0.2 micron filter and stored at −80.degree ° C.

Exemplary Pegylated IL-10 Synthetic Scheme No. 2. Mono-pegylated IL-10 is prepared using methoxy-PEG-aldehyde (PALD-PEG) as a linker (Inhale Therapeutic Systems Inc., Huntsville, Ala.; also available from NOF America Corp (Irvine, Calif.)). PALD-PEG can have molecular weights of 5 KDa, 12 KDa, or 20 KDa. IL-10 is dialyzed and diluted as described above, except the pH of the reaction buffer is between 6.3 and 7.5. Activated PALD-PEG linker is added to reaction buffer at a 1:1 molar ratio. Aqueous cyanoborohydride is added to the reaction mixture to a final concentration of 0.5 to 0.75 mM. The reaction is carried out at room temperature (18-25° C.) for 15-20 hours with mild agitation. The reaction is quenched with 1M glycine. Yields are analyzed by SE-HPLC. Mono-pegylated IL-10 is separated from unreacted IL-10, PEG linker and di-pegylated IL-10 by gel filtration chromatography and characterized by RP-HPLC and bioassay (e.g., stimulation of IL-10—responsive cells or cell lines).

Exemplary PEG-IL-10 Synthetic Scheme No. 3. IL-10 (e.g., rodent or primate) is dialyzed against 50 mM sodium phosphate, 100 mM sodium chloride pH ranges 5-7.4. A 1:1-1:7 molar ratio of 5K PEG-propyladehyde is reacted with IL-10 at a concentration of 1-12 mg/mL in the presence of 0.75-30 mM sodium cyanoborohydride. Alternatively the reaction can be activated with picoline borane in a similar manner. The reaction is incubated at 5-30° C. for 3-24 hours.

The pH of the pegylation reaction is adjusted to 6.3, 7.5 mg/mL of hIL-10 is reacted with PEG to make the ratio of IL-10 to PEG linker 1:3.5. The final concentration of cyanoborohydride is ~25 mM, and the reaction is carried out at 15° C. for 12-15 hours. The mono- and di-pegylated IL-10 are the largest products of the reaction, with the concentration of each at ~45-50% at termination. The reaction may be quenched using an amino acid such as glycine or lysine or, alternatively, Tris buffers. Multiple purification methods can be employed such as gel filtration, anion and cation exchange chromatographies, and size exclusion HPLC (SE-HPLC) to isolate the desired pegylated IL-10 molecules.

Exemplary Pegylated IL-10 Synthetic Scheme No. 4. IL-10 is dialyzed against 10 mM sodium phosphate pH 7.0, 100 mM NaCl. The dialyzed IL-10 is diluted 3.2 times to a concentration of about 0.5 to 12 mg/mL using the dialysis buffer. Prior to the addition of the linker, SC-PEG-12K (Delmar Scientific Laboratories, Maywood, Ill.), one volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to initiate the pegylation reaction. The reaction is carried out at 5° C. in order to control the rate of the reaction, and the reaction solution is mildly agitated. When the mono-pegylated IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction is 0.2 micron filtered and stored at −80° C.

Assays to Determine the Bioactivity of Modified Forms of IL-10

The present disclosure contemplates the use of any assays and methodologies known in the art for determining the bioactivity of the IL-10 molecules (e.g, PEG-IL-10) described herein. The MC/9 Cell Proliferation Assay described hereafter is representative, and not exclusionary.

MC/9 Cell Proliferation Assay. IL-10 administration to MC/9 cells (murine cell line with characteristics of mast cells available from Cell Signaling Technology; Danvers, Mass.) causes increased cell proliferation in a dose-dependent manner.

Thompson-Snipes, L. et al. ((1991) J. Exp. Med. 173: 507-10) describe a standard assay protocol in which MC/9 cells are supplemented with IL3+IL10 and IL3+IL4+IL10. Vendors (e.g., R&D Systems, USA; and Cell Signaling Technology, Danvers, Mass.) use the assay as a lot release assay for rhIL10. Those of ordinary skill in the art will be able to modify the standard assay protocol described in Thompson-Snipes, L. et al, such that cells are only supplemented with IL-10.

Identification of PEG-rhIL-10DS by Digestion with Endo Glu-C

In order to discern the integrity of pegylated recombinant human IL-10 Drug Substance (PEG-rhIL-10DS), PEG-rhIL-10DS was digested with Endo Glu-C, followed by reduction with DTT and analysis using RP-HPLC with UV detection. The PEG-rhIL-10DS comprised a mixture of mono-pegylated and di-pegylated IL-10 in a ratio of approximately 1:1, wherein pegylation occurs at the N-terminus. The PEG component of the PEG-IL-10 molecule had a molecular mass of approximately 5 kDa.

Initially, a theoretical digestion of PEG-rhIL-10DS and subsequent determination of the peptide masses were predicted using commercially-available software. Endo Glu-C digestions were undertaken where 0.1 mg of PEG-rhIL-10 in formulation matrix was mixed with 40 µg of enzyme for 6 hours at 25±2° C., followed by addition of 37 µl of 500 mM DTT for 1 hour at 37±2° C. The solution was then resolved over a Waters XBridge BEH300 C18, 3.5 mm, 2.1 mm×100 mm column (Waters Corp; Milford, Mass.), a HPLC system equipped with UV detection, autoinjector, gradient analytical pump, column heater and an appropriate data collection system. Peptide masses were determined by LC/MS. The theoretical peptide digest masses were congruent with observed peptide masses, indicating 100% digestion and illustrating that the method was suitable for an identity test.

The above-described peptide detection method was then qualified with a UV-based detection method employing the Empower software package (Empower Software Solutions; Orlando, Fla.). Compared to LC/MS methodology, the UV-based method was more robust and transferable.

PEG-rhIL-10 and rhIL-10 were then digested with Endo Glu-Ct, and a UV-detected map was generated. As depicted in the chromatogram set forth in FIG. 4, the Endo Glu-C digest yielded discrete peaks wherein the peptide map of rhIL-10 (dark trace) and PEG-rhIL-10 (light trace) yielded substantially similar traces. Thus, the Endo Glu-C peptidase provided robust results as to the identity (e.g., amino acid sequence) and stability of compositions comprising pegylated interleukin-10 and other pegylated interleukin-10—related molecules.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of confirming the amino acid sequence of a pegylated interleukin-10 (PEG-IL-10), comprising:
   fragmenting a test PEG-IL-10 with a glutamyl endopeptidase (Endo Glu-C), to yield a test plurality of peptides;
   separating peptide members of the test plurality of peptides by chromatography;
   analyzing said separated peptide members using ultraviolet absorption spectroscopy to provide a test PEG-IL-10 chromatogram;
   comparing the test PEG-IL-10 chromatogram to a reference standard chromatogram, said reference standard chromatogram generated by Endo Glu-C digestion of a reference standard PEG-IL-10, separating peptide members of the reference standard by chromatography, and analyzing said separated peptide members using ultraviolet absorption spectroscopy to provide the reference standard chromatogram;
   wherein the amino acid sequence of the test PEG-IL-10 is confirmed by the substantial equivalency of the retention time of the peaks of the test PEG-IL-10 chromatogram and the reference standard chromatogram.

2. The method of claim 1, wherein both the test and reference standard PEG-IL-10 is PEG-hIL-10.

3. The method of claim 1, wherein the chromatography is reverse phase high performance liquid chromatography.

4. The method of claim 1, wherein the test and reference standard PEG-IL-10 comprises a mixture of mono-pegylated and di-pegylated IL-10.

5. The method of claim 4, wherein the PEG component of the test PEG-IL-10 has a molecular mass from about 5kDa to about 20kDa.

* * * * *

SEQUENCE LISTING

```
<160> NUMBER OF SEQ ID NOS: 21

<210> SEQ ID NO 1
<211> LENGTH: 178
<212> TYPE: PRT
<213> ORGANISM: Homo sapiens

<400> SEQUENCE: 1

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 2
<211> LENGTH: 160
<212> TYPE: PRT
<213> ORGANISM: Homo sapiens

<400> SEQUENCE: 2

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80
```

```
Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 3
<211> LENGTH: 274
<212> TYPE: PRT
<213> ORGANISM: Artificial Sequence
<220> FEATURE:
<223> OTHER INFORMATION: synthetic polypeptide

<400> SEQUENCE: 3

Val Ile Leu Pro Asn Asn Asp Arg His Gln Ile Thr Asp Thr Thr Asn
1               5                   10                  15

Gly His Tyr Ala Pro Val Thr Tyr Ile Gln Val Glu Ala Pro Thr Gly
            20                  25                  30

Thr Phe Ile Ala Ser Gly Val Val Gly Lys Asp Thr Leu Leu Thr
        35                  40                  45

Asn Lys His Val Val Asp Ala Thr His Gly Asp Pro His Ala Leu Lys
    50                  55                  60

Ala Phe Pro Ser Ala Ile Asn Gln Asp Asn Tyr Pro Asn Gly Gly Phe
65                  70                  75                  80

Thr Ala Glu Gln Ile Thr Lys Tyr Ser Gly Gly Asp Leu Ala Ile
            85                  90                  95

Val Lys Phe Ser Pro Asn Glu Gln Asn Lys His Ile Gly Glu Val Val
            100                 105                 110

Lys Pro Ala Thr Met Ser Asn Asn Ala Glu Thr Gln Val Asn Gln Asn
            115                 120                 125

Ile Thr Val Thr Gly Tyr Pro Gly Asp Lys Pro Val Ala Thr Met Trp
130                 135                 140

Glu Ser Lys Gly Lys Ile Thr Tyr Leu Lys Gly Glu Ala Met Gln Tyr
145                 150                 155                 160

Asp Leu Ser Thr Thr Gly Gly Asn Ser Gly Ser Pro Val Phe Asn Glu
            165                 170                 175

Lys Asn Glu Val Ile Gly Ile His Trp Gly Gly Val Pro Asn Glu Phe
            180                 185                 190

Asn Gly Ala Val Phe Ile Asn Glu Asn Val Arg Asn Phe Leu Lys Gln
            195                 200                 205

Asn Ile Glu Asp Ile His Phe Ala Asn Asp Gln Pro Asn Asn Pro
    210                 215                 220

Asp Asn Pro Asp Asn Pro Asn Asn Pro Asp Asn Pro Asn Asn Pro Asp
225                 230                 235                 240

Glu Pro Asn Asn Pro Asp Asn Pro Asn Pro Asp Asn Pro Asp Asn
            245                 250                 255

Gly Asp Asn Asn Asn Ser Asp Asn Pro Asp Ala Ala His His His His
            260                 265                 270

His His
```

<210> SEQ ID NO 4
<211> LENGTH: 11
<212> TYPE: PRT
<213> ORGANISM: Artificial sequence
<220> FEATURE:
<223> OTHER INFORMATION: synthetic polypeptide

<400> SEQUENCE: 4

Tyr Gly Arg Lys Lys Arg Arg Gln Arg Arg Arg
1               5                   10

<210> SEQ ID NO 5
<211> LENGTH: 12
<212> TYPE: PRT
<213> ORGANISM: Artificial sequence
<220> FEATURE:
<223> OTHER INFORMATION: synthetic polypeptide

<400> SEQUENCE: 5

Arg Arg Gln Arg Arg Thr Ser Lys Leu Met Lys Arg
1               5                   10

<210> SEQ ID NO 6
<211> LENGTH: 27
<212> TYPE: PRT
<213> ORGANISM: Artificial sequence
<220> FEATURE:
<223> OTHER INFORMATION: synthetic polypeptide

<400> SEQUENCE: 6

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 7
<211> LENGTH: 33
<212> TYPE: PRT
<213> ORGANISM: Artificial sequence
<220> FEATURE:
<223> OTHER INFORMATION: synthetic polypeptide

<400> SEQUENCE: 7

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 8
<211> LENGTH: 16
<212> TYPE: PRT
<213> ORGANISM: Artificial sequence
<220> FEATURE:
<223> OTHER INFORMATION: synthetic polypeptide

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 9
<212> TYPE: PRT
<213> ORGANISM: Artificial sequence
<220> FEATURE:

```
<223> OTHER INFORMATION: synthetic polypeptide

<400> SEQUENCE: 9

Arg Lys Lys Arg Arg Gln Arg Arg Arg
1               5

<210> SEQ ID NO 10
<211> LENGTH: 8
<212> TYPE: PRT
<213> ORGANISM: Artificial sequence
<220> FEATURE:
<223> OTHER INFORMATION: synthetic polypeptide

<400> SEQUENCE: 10

Arg Lys Lys Arg Arg Gln Arg Arg
1               5

<210> SEQ ID NO 11
<211> LENGTH: 11
<212> TYPE: PRT
<213> ORGANISM: Artificial sequence
<220> FEATURE:
<223> OTHER INFORMATION: synthetic polypeptide

<400> SEQUENCE: 11

Tyr Ala Arg Ala Ala Ala Arg Gln Ala Arg Ala
1               5                   10

<210> SEQ ID NO 12
<211> LENGTH: 11
<212> TYPE: PRT
<213> ORGANISM: Artificial sequence
<220> FEATURE:
<223> OTHER INFORMATION: synthetic polypeptide

<400> SEQUENCE: 12

Thr His Arg Leu Pro Arg Arg Arg Arg Arg Arg
1               5                   10

<210> SEQ ID NO 13
<211> LENGTH: 11
<212> TYPE: PRT
<213> ORGANISM: Artificial sequence
<220> FEATURE:
<223> OTHER INFORMATION: synthetic polypeptide

<400> SEQUENCE: 13

Gly Gly Arg Arg Ala Arg Arg Arg Arg Arg Arg
1               5                   10

<210> SEQ ID NO 14
<211> LENGTH: 5
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(5)
<223> OTHER INFORMATION: amino acids 1-5 may be repeated n times where
      n is an an integer of at least one

<400> SEQUENCE: 14

Gly Ser Gly Gly Ser
1               5

<210> SEQ ID NO 15
```

```
<211> LENGTH: 4
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(4)
<223> OTHER INFORMATION: amino acids 1-4 may be repeated n times where
      n is an an integer of at least one

<400> SEQUENCE: 15

Gly Gly Gly Ser
1

<210> SEQ ID NO 16
<211> LENGTH: 4
<212> TYPE: PRT
<213> ORGANISM: Artificial sequence
<220> FEATURE:
<223> OTHER INFORMATION: synthetic polypeptide

<400> SEQUENCE: 16

Gly Gly Ser Gly
1

<210> SEQ ID NO 17
<211> LENGTH: 5
<212> TYPE: PRT
<213> ORGANISM: Artificial sequence
<220> FEATURE:
<223> OTHER INFORMATION: synthetic polypeptide

<400> SEQUENCE: 17

Gly Gly Ser Gly Gly
1               5

<210> SEQ ID NO 18
<211> LENGTH: 5
<212> TYPE: PRT
<213> ORGANISM: Artificial sequence
<220> FEATURE:
<223> OTHER INFORMATION: synthetic polypeptide

<400> SEQUENCE: 18

Gly Ser Gly Ser Gly
1               5

<210> SEQ ID NO 19
<211> LENGTH: 5
<212> TYPE: PRT
<213> ORGANISM: Artificial sequence
<220> FEATURE:
<223> OTHER INFORMATION: synthetic polypeptide

<400> SEQUENCE: 19

Gly Ser Gly Gly Gly
1               5

<210> SEQ ID NO 20
<211> LENGTH: 5
<212> TYPE: PRT
<213> ORGANISM: Artificial sequence
<220> FEATURE:
<223> OTHER INFORMATION: synthetic polypeptide

<400> SEQUENCE: 20

Gly Gly Gly Ser Gly
```

```
1               5

<210> SEQ ID NO 21
<211> LENGTH: 5
<212> TYPE: PRT
<213> ORGANISM: Artificial sequence
<220> FEATURE:
<223> OTHER INFORMATION: synthetic polypeptide

<400> SEQUENCE: 21

Gly Ser Ser Ser Gly
1               5
```